United States Patent
Mills

(10) Patent No.: US 6,872,541 B2
(45) Date of Patent: Mar. 29, 2005

(54) METHOD AND COMPOSITIONS FOR ANALYSIS OF PENTRAXIN RECEPTORS AS INDICATORS OF DISEASE

(75) Inventor: Rhonda Ann Mills, Miami Lakes, FL (US)

(73) Assignee: Coulter International Corp., Miami, FL (US)

( * ) Notice: Subject to any disclaimer, the term of this patent is extended or adjusted under 35 U.S.C. 154(b) by 287 days.

(21) Appl. No.: 09/915,892

(22) Filed: Jul. 25, 2001

(65) Prior Publication Data

US 2003/0022245 A1 Jan. 30, 2003

(51) Int. Cl.[7] .......................... C12Q 1/00; G01N 33/53; G01N 33/967
(52) U.S. Cl. ........................ 435/7.21; 435/7.1; 435/5
(58) Field of Search ...................... 435/4, 5, 7.1, 7.2, 435/7.21

(56) References Cited

U.S. PATENT DOCUMENTS

| | | | |
|---|---|---|---|
| 4,542,104 A | | 9/1985 | Stryer et al. |
| 5,171,846 A | | 12/1992 | Gupta |
| 5,221,628 A | * | 6/1993 | Anderson et al. |
| 5,272,257 A | | 12/1993 | Gupta |
| 5,547,931 A | * | 8/1996 | Potempa |
| 6,406,698 B1 | * | 6/2002 | Svehang et al. |

FOREIGN PATENT DOCUMENTS

| | | | |
|---|---|---|---|
| EP | 0411017 B1 | * | 3/1996 |
| WO | WO 99/60130 | * | 11/1999 |

OTHER PUBLICATIONS

Macy, et al., 1997, *Clin. Chem.* 43(1):52–8.
Custer, et al., 1990, *J. Immunol. Methods*, 128, 109–117.
Waggoner, et al., 1993, *Ann. N.Y. Acad. Sci.*, 677:185–193.
James, et al., 1982, *Ann. N.Y. Acad. Sci.*, 389:274–85.
Roederer et al, 1996, *Cytometry*, 24:191–197.
Mullenix, et al., 1994, *Mol. Immunol.*, 31(8):615–22.
Ziegler–Heitbrock, et al, 1996, *Eur. J. Immunol.*, 23(9):2053–8.
Ballou, et al., 1991, *Clin. Exp. Immunol.*, 84:329–335.
Ballou, et al., 1989, *J. Immunol.*, 142(8):2708–13.
R.B. Merrifield, 1963, *J. Amer. Chem. Soc.*, 85:2149–2154.
Kilpatrick, et al., 1991, *Immunol. Res.*, 10(1):43–53.

* cited by examiner

*Primary Examiner*—Leon B. Lankford, Jr.
*Assistant Examiner*—Ruth Davis
(74) *Attorney, Agent, or Firm*—Howson and Howson; Mitchell E. Alter

(57) ABSTRACT

A kit for assessing the level of pentraxin-binding moieties on particles in a biological sample containing a ligand comprising a pentraxin is useful in a method of assessing pentraxin-binding of particles for use in diagnosis of disease or abnormality. The method includes the steps of (a) exposing a biological test sample containing particles that comprise a pentraxin-binding receptor from a test subject to a ligand comprising a pentraxin in the presence of calcium; (b) determining quantitatively the level of binding between particles and ligand in said test sample; and (c) comparing the level of binding in said test sample to the level of binding in a control biological sample containing said particles from a healthy subject of the same species as the subject supplying the test sample. A change in the level of binding in said test sample from that of the control sample is indicative of disease or abnormality.

17 Claims, 22 Drawing Sheets

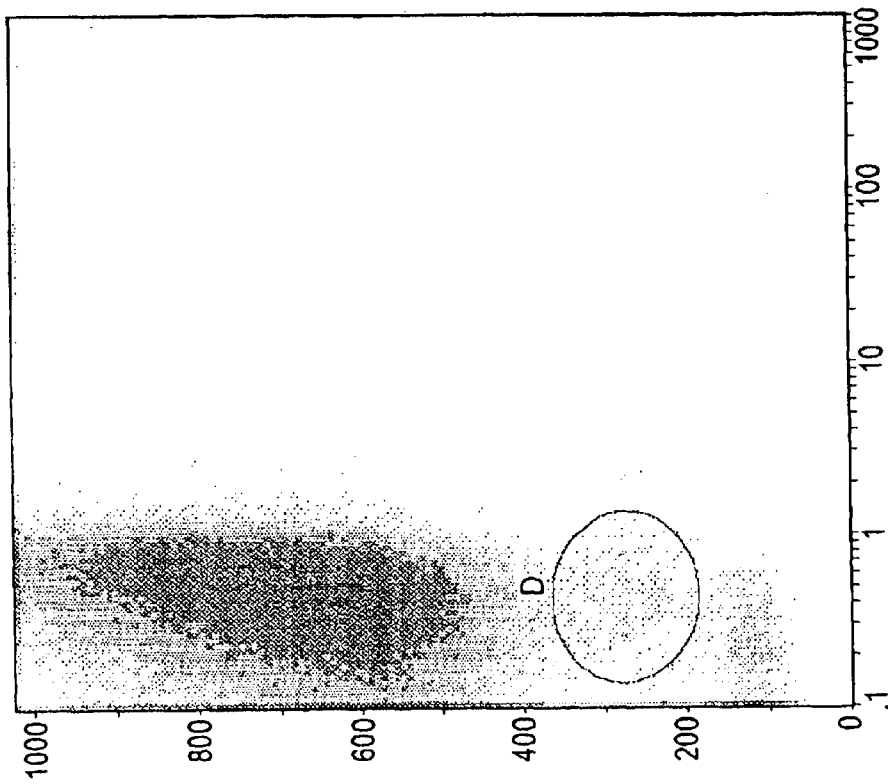
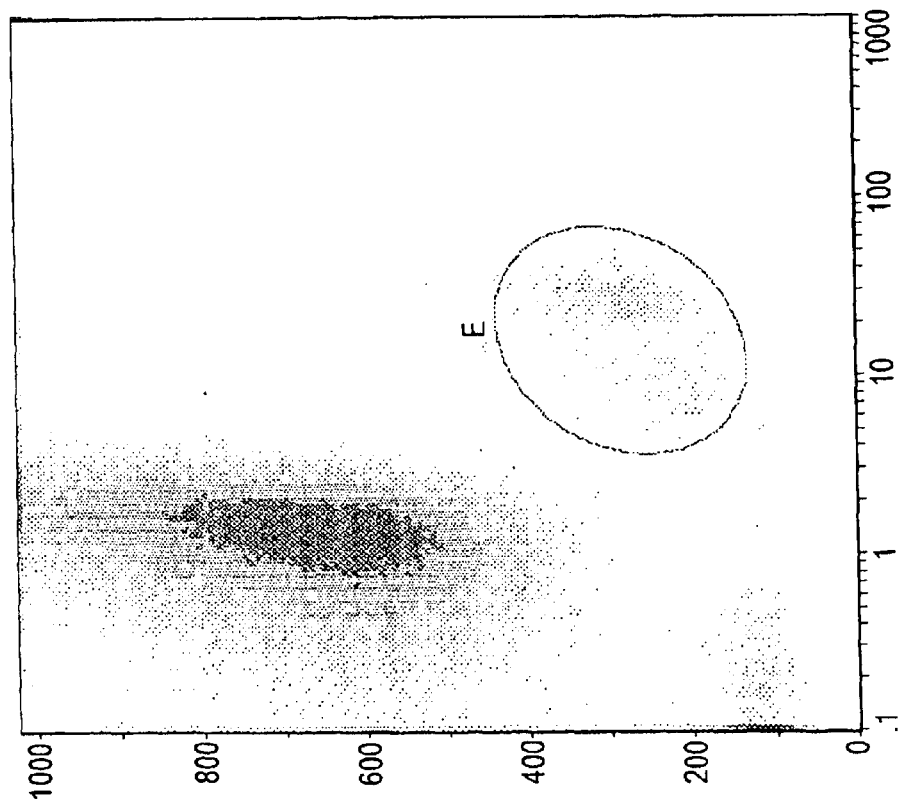

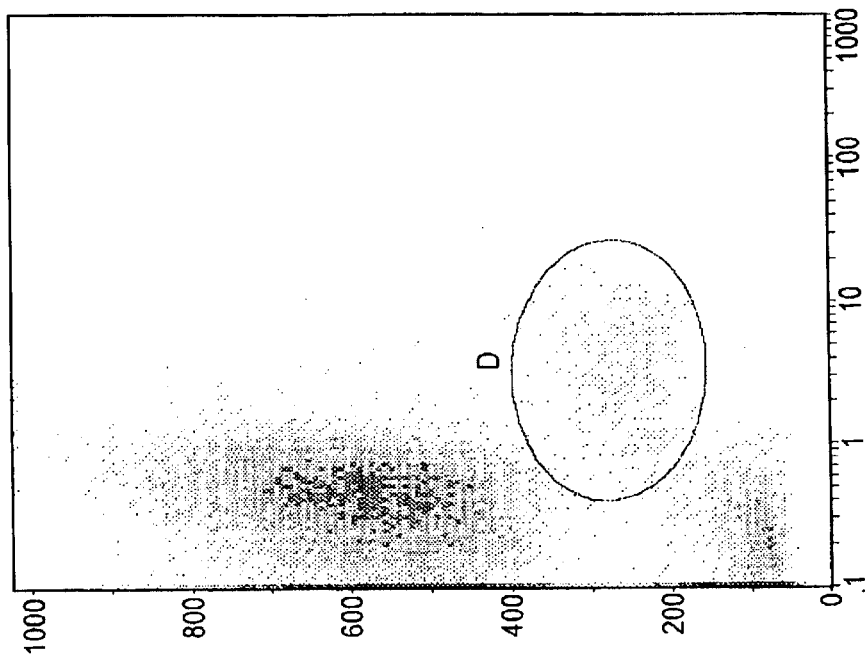
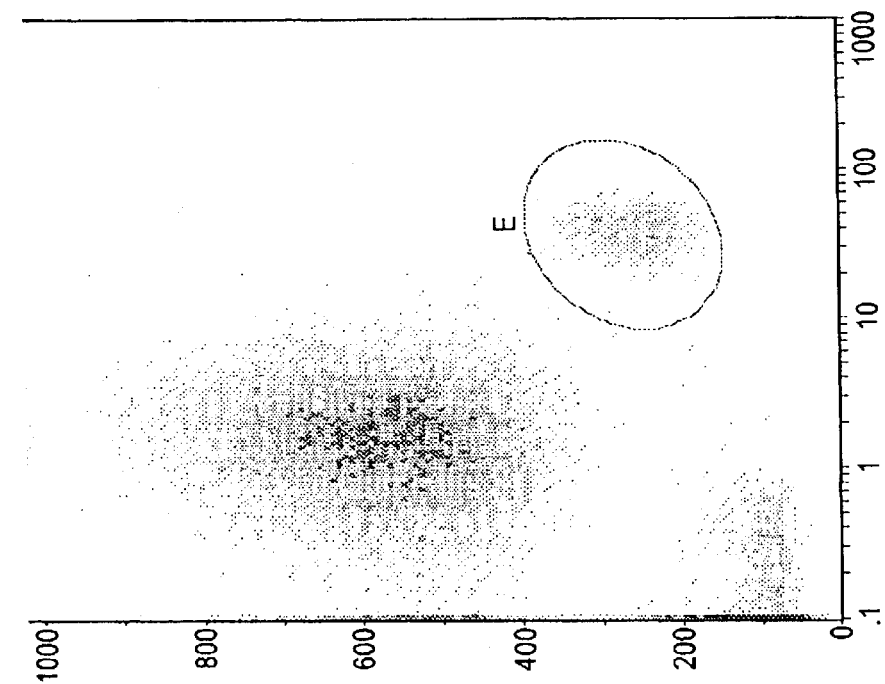

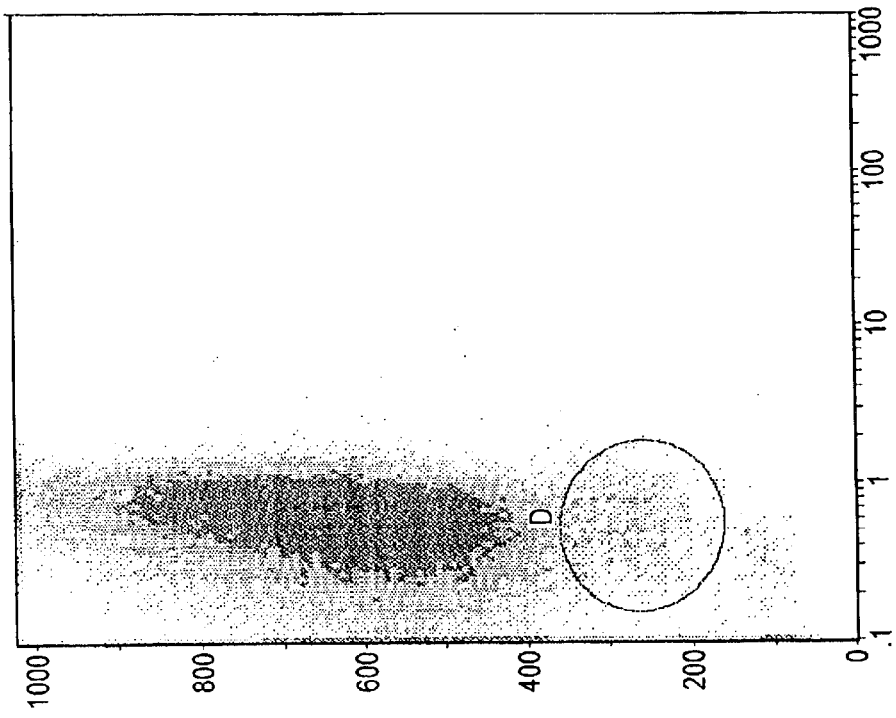
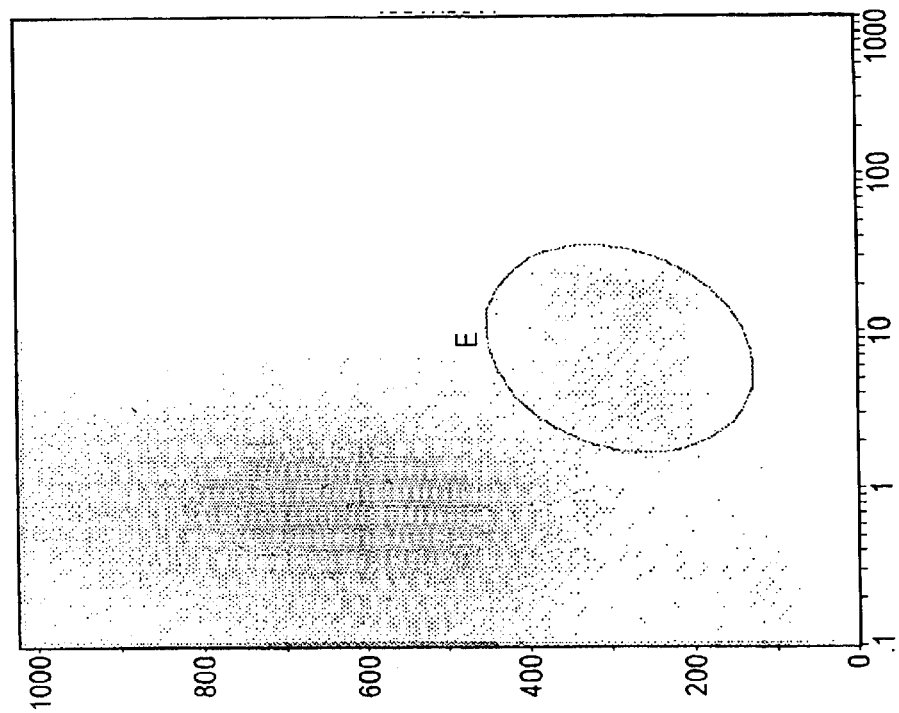

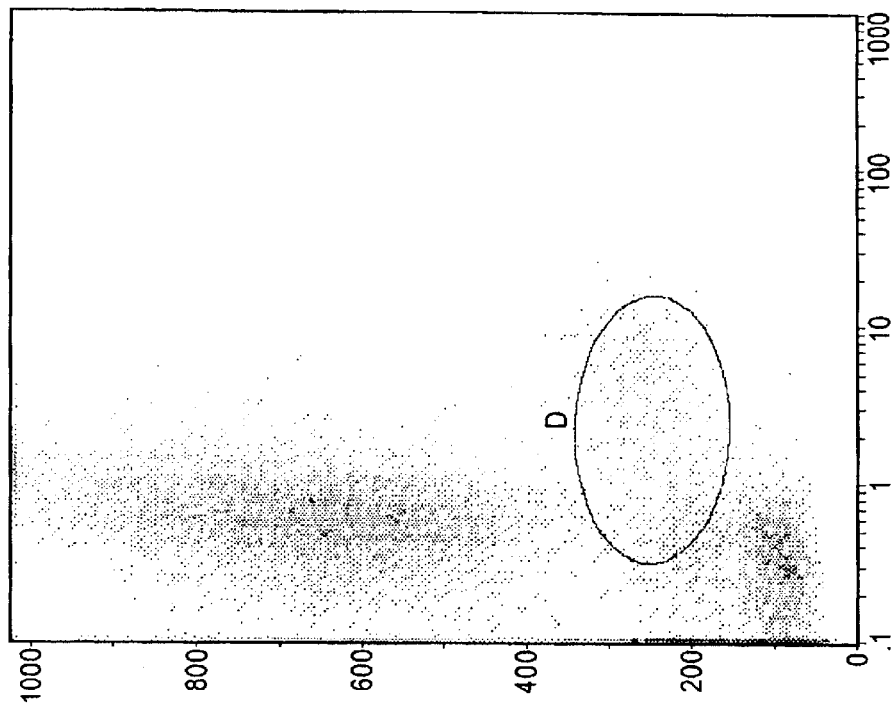
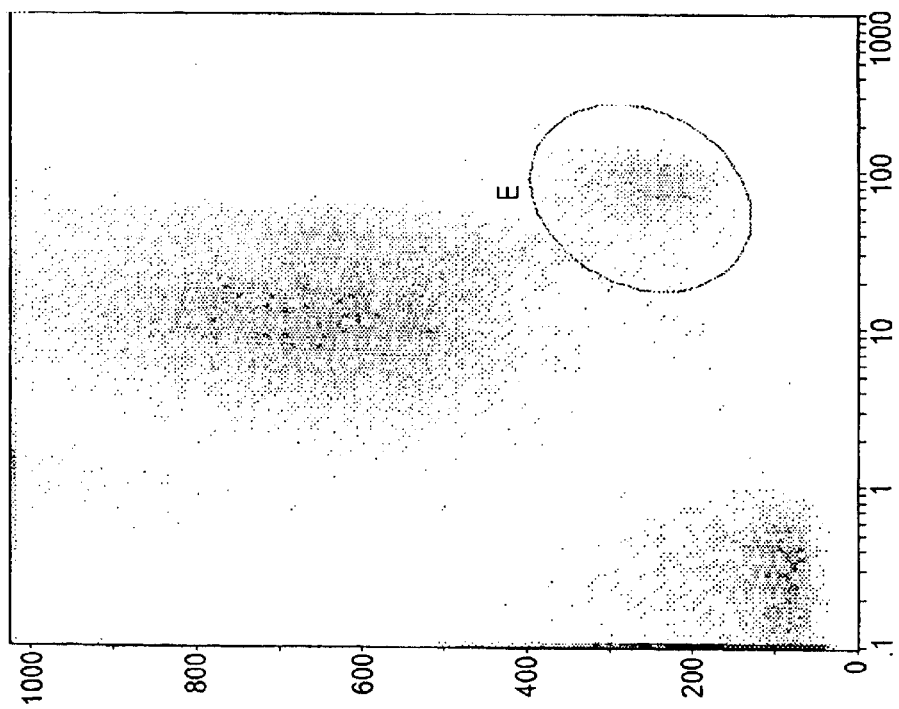

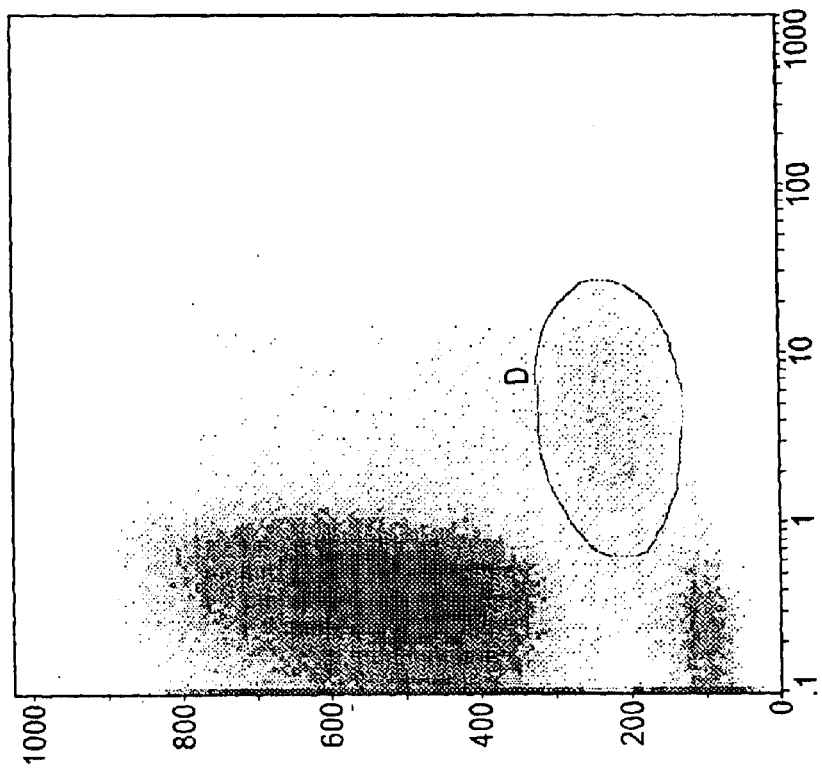
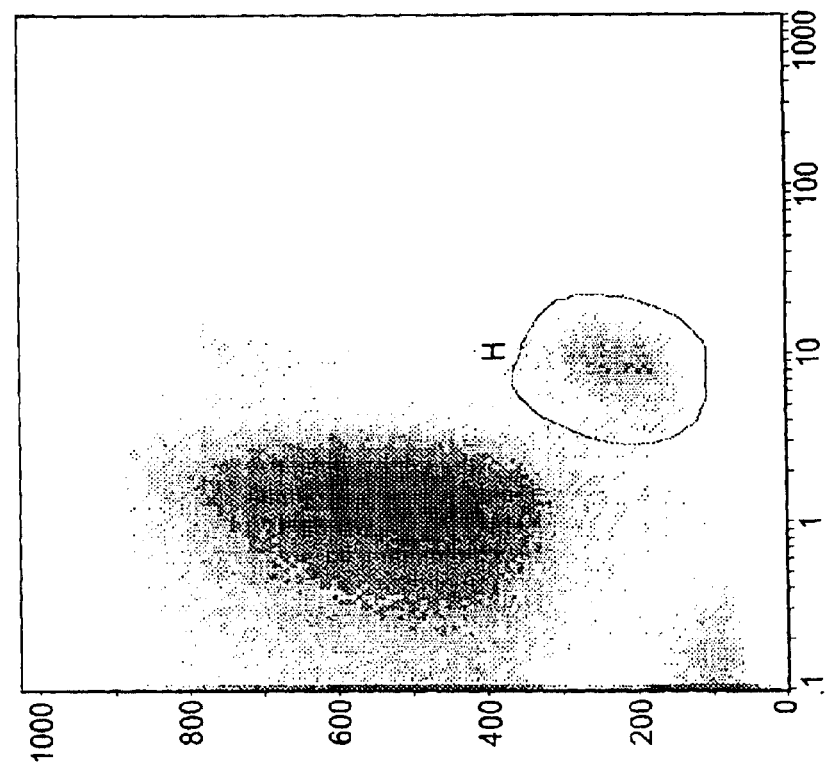

FIG. 2: Mean values for % monocytes, %CRP+ and plasma CRP concentration of each patient sample within the generalized category NT = Not Tested

| Initial Dx | Confirmed Dx | % Monos | % CRPR+ | [CRP] ug/mL |
|---|---|---|---|---|
| | Inflammation | | | |
| grans | acute pancreatitis | 2.8 | 10.5 | 11.2 |
| grans | acute pancreatitis | 3.6 | 31.0 | NT |
| grans | acute rheumatic endocarditis | 2.5 | 33.9 | 91.3 |
| bands | decubitus ulcer | 2.0 | 5.5 | NT |
| ANA | lupus cerebritis | 3.1 | 42.1 | 5.7 |
| grans | chronic airway obstruction | 1.7 | 31.4 | NT |
| ANA | Ascites | 9.8 | 56.8 | 3.9 |
| | Cardiac | | | |
| AMI | angina | 3.8 | 70.1 | 29.3 |
| AMI | chest pain | 3.3 | 62.0 | NT |
| AMI | chest pain | 7.5 | 73.3 | 1.4 |
| AMI | chest pain | 5.3 | 77.2 | 2.3 |
| grans | congestive heart failure | 7.3 | 12.5 | 63.8 |
| RA | congestive heart failure | 4.2 | 55.6 | 7.3 |
| RA | congestive heart failure | 7.5 | 61.7 | 10.8 |
| grans | congestive heart failure | 2.8 | 63.6 | NT |
| ANA | congestive heart failure | 3.4 | 69.4 | 16.4 |
| RA | congestive heart failure | 4.6 | 75.1 | 15.6 |
| RA | congestive heart failure | 6.9 | 76.9 | 25.2 |
| | Cancer | | | |
| grans | breast cancer | 0.8 | 22.8 | NT |
| grans | breast cancer | 3.0 | 51.0 | NT |
| ANA | cancer in situ | 4.7 | 18.8 | 33.3 |
| grans | colon cancer | 3.5 | 11.0 | NT |
| grans | desmoid tumor, p. aeruginosa, candid | 0.6 | 4.9 | NT |
| lymphoma | large cell lymphoma | 3.0 | 17.8 | 22.5 |
| bands | lymphoma | 9.0 | 21.6 | 15.4 |
| leukemia | Lymphoma | 2.1 | 25.6 | 11.5 |
| bands | malignant neoplasia breast | 9.6 | 38.6 | NT |
| bands | multiple myeloma | 0.8 | 6.0 | NT |
| RA | hyperplasia | 6.2 | 69.4 | 19.4 |
| | Hemorrhage | | | |
| bands | volume depletion | 5.9 | 84.5 | 375.8 |
| bands | pregnancy complications | 4.7 | 63.3 | 17.3 |
| bands | traumatic brain hemorrhage | 7.2 | 73.9 | 409.2 |
| grans | subarachnoid hemorrhage | 1.3 | 64.7 | 87.0 |
| grans | open wound anterior abdomen | 2.6 | 62.1 | 39.5 |

| Initial Dx | Confirmed Dx | % Monos | % CRPR+ | [CRP] ug/mL |
|---|---|---|---|---|
| | Infection | | | |
| bands | varicella | 0.9 | 26.0 | NT |
| bands | septicemia | 1.8 | 26.5 | NT |
| grans | septicemia | 2.0 | 41.7 | 11.2 |
| bands | pulmonary nocardiosis | 5.4 | 9.0 | 205.9 |
| grans | T. glabrata/Fever | 0.8 | 7.7 | NT |
| grans | pneumonia | 3.1 | 7.2 | 85.4 |
| grans | pneumonia | 1.9 | 7.8 | 26.6 |
| bands | pneumonia | 2.9 | 28.4 | NT |
| grans | Pneumonia | 2.5 | 29.7 | NT |
| grans | pneumonia | 8.3 | 39.1 | 39.3 |
| bands | pneumonia | 2.7 | 57.6 | 108.3 |
| bands | urinary tract infection | 1.7 | 24.0 | 69.8 |
| ANA | pneumonia | 1.3 | 67.0 | 60.4 |
| | Miscellaneous | | | |
| grans | abdominal pain | 1.3 | 54.3 | NT |
| bands | elevated creatinine | 2.2 | 47.0 | 3.2 |
| bands | elevated creatinine | 2.4 | 68.7 | NT |
| grans | ileostomy | 0.9 | 49.9 | NT |
| grans | IUP @ 40 weeks | 2.0 | 75.8 | NT |
| grans | liver transplant/abdominal pain | 3.0 | 55.4 | 3.2 |
| grans | Liver TSPL, fever,yeast | 6.2 | 48.3 | NT |
| grans | Liver TSPL, few gram - rods, | 3.2 | 73.6 | NT |
| bands | lung disease | 7.4 | 45.9 | 73.6 |
| grans | respiratory failure | 2.1 | 77.2 | 51.6 |
| grans | vasculite hypertension | 5.4 | 58.0 | 6.9 |
| grans | multiple sclerosis | 2.7 | 26.6 | NT |
| ANA | SLE | 3.2 | 86.0 | 66.6 |
| bands | diabetes | 3.3 | 61.4 | 199.2 |
| grans | cardiac transplant/hepatitis | 2.1 | 12.3 | 28.2 |
| ANA | cirrhosis | 4.2 | 25.1 | 24.9 |
| ANA | cirrhosis | 7.9 | 32.4 | 7.5 |
| ANA | cirrhosis | 5.0 | 38.0 | 27.9 |
| ANA | cirrhosis | 2.9 | 40.0 | 8.4 |
| ANA | cirrhosis | 4.9 | 77.4 | 5.3 |
| bands | cocaine abuse | 3.5 | 32.7 | 24.6 |

FIG. 4

| Category | %CRP+ | Cluster | Diagnosis |
|---|---|---|---|
| Miscellaneous | 86.0 | 2 | SLE |
| Hemorrhage | 84.5 | 2 | volume depletion |
| Miscellaneous | 77.4 | 2 | cirrhosis |
| Cardiac | 77.2 | 2 | chest pain |
| Miscellaneous | 77.2 | 2 | respiratory failure |
| Cardiac | 76.9 | 2 | CHF |
| Miscellaneous | 75.8 | 2 | IUP |
| Cardiac | 75.1 | 2 | CHF |
| Hemorrhage | 73.9 | 2 | brain hemorrhage |
| Miscellaneous | 73.6 | 2 | liver tspl, few gram- rods |
| Cardiac | 73.3 | 2 | chest pain |
| Cardiac | 70.1 | 2 | angina |
| Cardiac | 69.4 | 2 | CHF |
| Cancer | 69.4 | 2 | hyperplasia, RA |
| Miscellaneous | 68.7 | 2 | elevated creatinine |
| Infection | 67.0 | 2 | pneumonia, ANA |
| Hemorrhage | 64.7 | 3 | subarachnoid hemorrhage |
| Cardiac | 63.6 | 3 | CHF |
| Hemorrhage | 63.3 | 3 | pregnancy complications |
| Hemorrhage | 62.1 | 3 | open wound |
| Cardiac | 62.0 | 3 | chest pain |
| Cardiac | 61.7 | 3 | CHF |
| Miscellaneous | 61.4 | 3 | diabetes |
| Miscellaneous | 58.0 | 3 | vasculite hypertension |
| Infection | 57.6 | 3 | pneumonia |
| Inflammation | 56.8 | 3 | ascites |
| Cardiac | 55.6 | 3 | CHF |
| Miscellaneous | 55.4 | 3 | liver tspl |
| Miscellaneous | 54.3 | 3 | abdominal pain |
| Cancer | 51.0 | 3 | breast cancer |
| Miscellaneous | 49.9 | 3 | ileostomy |
| Miscellaneous | 48.3 | 3 | liver tspl, fever, yeast |
| Miscellaneous | 47.0 | 3 | elevated creatinine |

| Category | %CRP+ | Cluster | Diagnosis |
|---|---|---|---|
| Miscellaneous | 45.9 | 4 | lung disease |
| Inflammation | 42.1 | 4 | lupus cerebritis |
| Infection | 41.7 | 4 | septicemia |
| Miscellaneous | 40.0 | 4 | cirrhosis |
| Infection | 39.1 | 4 | pneumonia |
| Cancer | 38.6 | 4 | breast cancer |
| Miscellaneous | 38.0 | 4 | cirrhosis |
| Inflammation | 33.9 | 4 | acute rheumatic endocarditis |
| Miscellaneous | 32.7 | 4 | cocaine abuse |
| Miscellaneous | 32.4 | 4 | cirrhosis |
| Inflammation | 31.4 | 4 | ulcer |
| Inflammation | 31.0 | 4 | acute pancreatitis |
| Infection | 29.7 | 4 | pneumonia |
| Infection | 28.4 | 4 | pneumonia |
| Miscellaneous | 26.6 | 4 | Multiple sclerosis |
| Infection | 26.5 | 4 | septicemia |
| Infection | 26.0 | 4 | varicella |
| Cancer | 25.6 | 4 | lymphoma |
| Miscellaneous | 25.1 | 4 | cirrhosis |
| Infection | 24.0 | 4 | UTI |
| Cancer | 22.8 | 1 | breast cancer |
| Cancer | 21.6 | 1 | lymphoma |
| Cancer | 18.8 | 1 | cancer in situ |
| Cancer | 17.8 | 1 | lymphoma |
| Cardiac | 12.5 | 1 | CHF |
| Miscellaneous | 12.3 | 1 | cardiac tspl/hepatitis |
| Cancer | 11.0 | 1 | colon cancer |
| Inflammation | 10.5 | 1 | acute pancreatitis |
| Infection | 9.0 | 1 | pulmonary nocardiosis |
| Infection | 7.8 | 1 | pneumonia |
| Infection | 7.7 | 1 | T. glabrata; fever |
| Infection | 7.2 | 1 | pneumonia |
| Cancer | 6.0 | 1 | myeloma |
| Inflammation | 5.5 | 1 | chronic airway obstruction |
| Cancer | 4.9 | 1 | desmoid tumor, p aeroginosa |

%CRP+ Monocytes vs. K-Means Cluster

Log CRP vs. K-Means Cluster

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: synthetic protein
<220> FEATURE:
<221> NAME/KEY: MISC_FEATURE
<222> LOCATION: (2)..(2)

```
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Ser or Thr
<220> FEATURE:
<221> NAME/KEY: MISC_FEATURE
<222> LOCATION: (7)..(7)
<223> OTHER INFORMATION: Xaa can be any amino acid

<400> SEQUENCE: 1

His Xaa Cys Xaa Xaa Trp Xaa Ser
 1               5

<210> SEQ ID NO 2
<211> LENGTH: 206
<212> TYPE: PRT
<213> ORGANISM: human CRP

<400> SEQUENCE: 2

Gln Thr Asp Met Ser Arg Lys Ala Phe Val Phe Pro Lys Glu Ser Asp
 1               5                   10                  15

Thr Ser Tyr Val Ser Leu Lys Ala Pro Leu Thr Lys Pro Leu Lys Ala
                20                  25                  30

Phe Thr Val Cys Leu His Phe Tyr Thr Glu Leu Ser Ser Thr Arg Gly
            35                  40                  45

Tyr Ser Ile Phe Ser Tyr Ala Thr Lys Arg Gln Asp Asn Glu Ile Leu
        50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205
```

METHOD AND COMPOSITIONS FOR ANALYSIS OF PENTRAXIN RECEPTORS AS INDICATORS OF DISEASE

BACKGROUND OF THE INVENTION

The present invention relates to improved methods and compositions for the identification and quantitation of receptors on the surfaces of certain hematological cells. More particularly, the present invention relates to a simple rapid diagnostic method for the indication of bacterial infection, disease or immune disorder in mammals.

Pentraxins include, among other proteins, C-reactive protein (CRP), that was originally identified as a serum factor responsible for the precipitation of 'acute phase' patient sera with the somatic C polysaccharide (CPS) of pneumococcal cell walls. CRP has been shown to participate in reactions of precipitation, agglutination, opsonization and complement activation. These properties have been reproduced over the years in different laboratories. Conflicting reports of suppression, stimulation or chemoattraction of polymorphonuclear leukocytes (PMN) or monocytes, as well as the activation or inhibition of platelets by CRP have yet to be resolved.

Human CRP is a pentameric protein composed of identical 206 amino acid subunits (SEQ ID NO: 2), each having a molecular weight of 23,017 daltons that associate by non-covalent bonds (Mullenix and Mortensen, 1994 *Mol. Immunol.*, 31(8):615-22). CRP can be dissociated to subunits by 8M urea or mild alkaline conditions only in the absence of calcium A single intramolecular disulfide bond links the two half-cysteines at Cys36 and Cys98. Human CRP is normally present in trace amounts in serum, e.g., 0.8–3 g/mL. However, during infection and inflammation, levels can increase a 1,000-fold in response to specific cytokines.

The single copy human CRP gene has been sequenced (Kilpatrick and Volanakis, 1991 *Immunol. Res.*, 10(1) :43–53). It contains two exons, one that encodes the signal peptide and the first two amino acids while the second contains the code for the remaining 204 amino acids and a long (1.2 kbp) 3' untranslated region (UTR). No differences in coding regions have been found in libraries but the poly(GT) length of the intron exhibits polymorphic variation with three alleles containing 15, 19 or 22 repeats. CRP maps to chromosome 1 region q21 to q25.

CRP has been previously noted to bind to the cell walls of many bacteria, fungi and nematodes via the cell wall structural component phosphorylcholine (PC). In the presence of calcium, the primary ligand for CRP is PC. CRP binds its ligand, PC, at $1.9 \times 10^{-5}$ M. Though PC is also a major component of mammalian cell membranes, CRP will bind to these membranes only under conditions that disturb the normal bilayer architecture. Many of the biological activities ascribed to CRP are initiated by binding ligands via the single PC-binding site within each subunit. Other reported ligands for CRP include small nuclear ribonucleoproteins (snRNP), fibronectin, lamnin, chromatin and histones.

The presence of CRP receptors (CRP-R) has been proposed for lymphocytes, NK cells, monocyte/macrophages and neutrophils. However, much of the prior art on CRP-R is conflicting. For example, reports of CRP-R on lymphocytes have implied an association with Fcγ receptors (FcγR) and a requirement for $Ca^{2+}$ in conjunction with a CRP-PC complex. An increase in CRP-bearing lymphocytes during certain disease states has been reported (James, et al., 1982 *Ann. NY. Acad. Sci.*, 389:274–85). From 1983 to 1991 various laboratories have reported the surface expression of CRP on lymphocytes along with de novo synthesis. Thus, the presence of a CRP-R on lymphocytes or surface expression of CRP has yet to be confirmed.

More recently, there have been reports of an inducible CRP receptor on PMA-stimulated neutrophils or a receptor for CRP on polymorphonuclear leukocytes (PMN) or neutrophils. It was reported that approximately 36% of resting PMN bound aggregated CRP compared to 93% when stimulated with PMA (Zeller, et al., 1986) and that 8% of the lymphocytes and 70% of the monocytes also bound aggregated CRP as detected by FITC-conjugated F(ab')₂ fragments of anti-CRP. Aggregated human IgG inhibited any binding by CRP leading to the suggested involvement of the Fc receptor. Still other reports indicated that both calcium and magnesium were necessary for binding to neutrophils. A CRP receptor on monocytes has been demonstrated in many laboratories under a variety of conditions. Approximately 40% of the peripheral blood monocytes and some mouse macrophage cell lines were reported to bind complexed CRP. The existence of a CRP-like determinant was reported on peripheral blood monocytes using polyclonal antibodies to CRP. Some papers have concluded that CRP-R is not FcγR, but may be associated with it.

Specific binding of radiolabeled CRP to isolated human peripheral blood monocytes (Ballou, et al., 1989 J. Immunol., 142(8):2708–13) was reported with a dissociation constant of about $10^{-7}$M, a requirement for calcium, an optimal pH of 7.4, and a lack of inhibition with human IgG. Other reports noted that an average of 67±12% of monocytes bound bCRP. Various publications in the 1990's have ascribed generation of $H_2O_2$ production, tumoricidal activity, induction of inflammatory cytokines, tissue factor and monocyte chemoattractant protein-1 to the internalization of the CRP receptor-bound ligand with subsequent degradation in human promonocyte U937 cells. Though there have been some reports of an increase in CRP-bearing lymphocytes during certain disease states, there have been no investigations of CRP binding to monocytes in any disease or its correlation to plasma CRP concentration.

Despite the considerable wealth of publications concerning CRP and its putative receptor(s), no biological role for C-reactive protein, the prototypic pentraxin, has been positively identified. The very nature and existence of the receptor is still under debate. Thus, there remains a need in the art for methods and compositions useful in the analysis of pentraxin-binding receptors in the presence of biological samples for the diagnosis of disease.

BRIEF SUMMARY OF THE INVENTION

In one aspect, the present invention provides a kit for assessing the level of pentraxin-binding moieties on particles in a biological sample of a test subject. Abnormal levels of such moieties are indicative of disease or abnormality associated with disease states. The kit contains, primarily, a ligand comprising a pentraxin. In one desirable embodiment, the pentraxin is mammalian C-reactive protein, or a fragment thereof. In another embodiment, the kit contains an additional ligand that binds to a cell surface receptor that is not pentraxin-binding. In some embodiments, the kit contains one or more detectable markers for labeling the pentraxin ligand and/or the additional ligand.

In another aspect, the invention provides a method of assessing pentraxin-binding of particles for use in diagnosis of disease or abnormality. The method involves exposing a biological test sample containing particles that comprise a pentraxin-binding receptor from a test subject to a ligand comprising a pentraxin in the presence of calcium. Thereafter the level of binding between particles and ligand in said test sample is determined quantitatively. The level of binding in said test sample is compared to the level of binding in a control biological sample containing said particles from a healthy subject of the same species as the subject supplying the test sample. A change in the level of binding in said test sample from that of the control sample is indicative of disease or abnormality.

In yet a further aspect, the invention provides an analysis instrument that comprises an integrated computer program that implements the method described above.

Other aspects and advantages of the present invention are described further in the following detailed description of the preferred embodiments thereof

BRIEF DESCRIPTION OF THE DRAWINGS

FIG. 1A is a side scatter (SS) vs. fluorescence histogram of inflammation showing the expression of CD33.

FIG. 1B is an SS vs. fluorescence histogram of the patient of FIG. 1A showing the expression of bCRP:SA-DTAF.

FIG. 1D is a SS vs. fluorescence histogram of a cardiac sample showing the expression of CD64.

FIG. 1E is a SS vs. fluorescence histogram of the patient of FIG. 1D showing the expression of bCRP:SA-DTAF.

FIG. 1J is a SS vs. fluorescence histogram of a pneumonia patient showing expression of CD33.

FIG. 1K is a SS vs. fluorescence histogram for the patient of FIG. 1J showing expression of bCRP:SA-DTAF.

FIG. 1M is a SS vs. fluorescence histogram of a hemorrhage sample showing expression of CD64.

FIG. 1N is a SS vs. fluorescence histogram for the patient of FIG. 1M showing expression of bCRP:SA-DTAF.

FIG. 1O is a histogram for the patient of FIG. 1M, showing monocytes (bitmapped) brought into an events vs. bCRP:SA-DTAF fluorescence histogram. Gray peak and open peak are as described in FIG. 1C.

FIG. 1P is a SS vs. fluorescence histogram of a systemic lupus erythematosis sample showing expression of CD33.

FIG. 1Q is a SS vs. fluorescence histogram for the patient of FIG. 1P showing expression of bCRP:SA-DTAF.

FIG. 2 is a table showing the mean values for % monocytes, % CRP+ and plasma CRP concentration of each patient sample within the general category.

FIG. 4 is a tabular breakdown of cluster analysis contrasted with the general disease categories.

DETAILED DESCRIPTION OF THE INVENTION

Figure 1C:
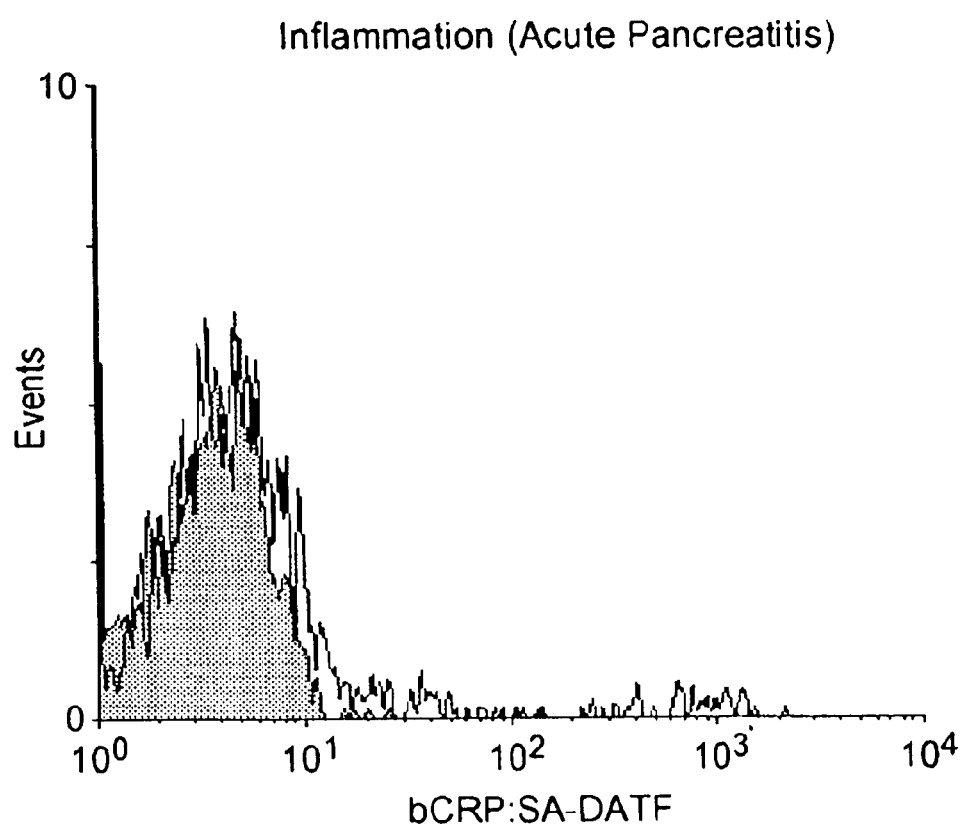
FIG. 1C is a histogram of the patient of FIG. 1A, showing monocytes (bitmapped) brought into an events vs. bCRP:SA-DTAF fluorescence histogram. Gray peak indicates negative bHSA control binding, open peak describes CRP positive monocyte events.

The present invention provides a novel and improved method for detecting, analyzing and identifying certain disease states based on the binding of a pentraxin ligand to particles bearing a pentraxin-binding moiety, e.g., a receptor or epitope that binds to a calcium-induced native pentraxin conformation. In certain disease states, the quality and quantity of such binding is altered, e.g., the binding of CRP to peripheral blood monocytes through a mechanism that does not involve phosphorylcholine. Compositions for identifying the alteration in a diagnostic method are disclosed.

A. Components Useful in the Compositions and Methods of This Invention

1. Ligand

By "ligand" is meant a moiety or binding partner that binds to a receptor. As defined herein, ligands include various agents that detect and react with one or more specific receptors. Ligands inside a cell are made accessible or brought to the surface by some process such as translocation, permeabilization, electroporation, etc. Methods useful for construction of such ligands are known to those of skill in the art. All such ligands are characterized by the desired ability to bind the specified receptor on a population of particles. In one preferred embodiment, the ligand of the invention is a component that preferentially binds to all or a portion of a cell surface receptor.

The present invention refers to two types of ligand: (a) those that include a pentraxin and (b) an additional ligand that does not bind a pentraxin receptor.

By "pentraxin" as used herein is meant a naturally-occurring protein or polypeptide that is a member of the pentraxin family or a synthetic, non-naturally occurring protein or polypeptide characterized by the amino acid motif His-Xxx-Cys-Xxx-Ser/Thr-Trp-Xxx-Ser (SEQ ID NO: 1), cyclic symmetry within a single plane and calcium-dependent binding. Exemplary naturally-occurring pentraxins include C-reactive protein (CRP), serum amyloid P (SAP), TNF-stimulated gene 14 (TSG-14 or PTX3), neuronal pentraxin 1 (NPR1), neuronal pentraxin 2 (NPR2), guinea pig apexin/p50, and rat neural activity-regulated pentraxin (narp). Other proteins or polypeptides referred to as pentraxins are those homologous to the above-identified pentraxins and containing the pentraxin motif SEQ ID NO: 1 and two conserved Cys. Preferably, these homologous polypeptides exhibit at least approximately 25% identity to human CRP on an amino acid level. The term pentraxin also encompasses fragments of the naturally occurring proteins that exhibit the biological activity of binding to cell populations through a mechanism that does not involve phosphorylcholine.

By "additional ligand" is meant a protein or polypeptide that binds a cell-surface receptor that does not bind pentraxin. Such additional ligands can include, for example, certain ligands that bind receptors on mammalian hematological cells. Examples of such ligands useful in the methods and composition of this invention include, without limitation, CD64, CD14, CD16, CD45RA, CD33, CD142 and HLA-DR.

2. Receptors

Receptors are defined generally by reference to the ligands they bind. Generally, a receptor is an antigen or protein or a portion thereof, that is capable of binding to a specified ligand. Most receptors are located on the surface of a particle. By "pentraxin-binding receptor" is meant an antigen or protein or a portion thereof, that is capable of binding to a pentraxin, and is normally located on the surface of a particle.

By non-pentraxin-binding receptor is meant an antigenic receptor that binds to another ligand. For example, receptors have been identified among the more than 200 antigens identified on the surface of hematological cells [A. N. Barclay et al, The Leukocyte Antigen Facts Book, 2nd edit., Academic Press, San Diego, Calif., publ. (1997), section II, pp. 132–593]. These include, without limitation, receptors for CD16b, CD14, CD24, CD48, CD52, CD55, CD59, CD66b, CD66c, CD73, CD87, CD90, gp42, LY-6, RT 6, and SCA-2. Receptors for CD64, CD14, CD16, CD45RA, CD33, CD142 and HLA-DR are included in this definition.

3. Samples and Particles

As used herein, the term "biological sample" refers to a body fluid or tissue, preferably of mammalian origin. Even more preferably, such body tissue or fluid is of human origin. The body fluid can include, without limitation, whole blood, peripheral blood, synovial fluid, cerebrospinal fluid, saliva, urine, or other fluid secretion. The term "tissue" can include, without limitation, bone marrow and lymph node, as well as samples of other tissues. Alternatively, the sample may be a cell line, such as the monocytic cell lines THP-1, U937, and KG-1a.

Depending on the nature of the particle, the sample may also include a physiologically-acceptable medium for the particles, e.g., saline, buffers or plant media.

As described herein, the term "particles" includes cells from mammalian and non-mammalian sources. For example, in one embodiment of the methods and kits of this invention, the particles are mammalian hematological or blood cells. In another embodiment, the particles are cell lines established from mammalian or non-mammalian cells. In still another embodiment, the particles are bacterial cells. Specifically excluded from the term "particles" are viruses. Exemplary "particles" include, without limitation, leucocytes, mast cells, macrophages, progenitor cells, platelets, endothelial cells, fibroblasts, neurons, microglial cells, and bacterial cells. The present invention is described specifically below using mammalian blood cells, specifically human white blood cells, as the particles.

4. Markers

As used herein, the term "marker" generally refers to a molecule, preferably proteinaceous, but also a small chemical molecule that is capable, acting alone, or in concert with other molecules or proteins, of providing a signal, that is detectable either directly or indirectly. In this invention, the marker is associated with the ligand containing a pentraxin and/or the same or preferably a different marker is associated with each additional non-pentraxin-binding ligand. For example, a detectable marker can be a fluorescent label, a luminescent label, a radiolabel, or a chemiluminescent label. A marker can be an enzyme that interacts with a substrate to produce the detectable signal. Another marker embodiment can be a protein that is detectable by antibody binding or by binding to a suitably labeled ligand.

In one embodiment, preferred markers enable detection by emitting a detectable signal of a particular wavelength upon excitation by a laser. Phycobiliproteins, tandem dyes, certain fluorescent proteins, small chemical molecules, and certain molecules detectable by other means can all be considered markers for flow cytometry analyses. See, e.g., the markers listed in *Handbook of Fluorescent Probes and Research Chemicals*, 6th Ed., R. P. Haugland, Molecular Probes, Inc., Eugene, Oreg. (1996). "Phycobiliproteins" are a family of macromolecules found in red algae and blue-green algae. The biliproteins (the term "biliproteins" is equivalent to the term "phycobiliprotein") have a molecular weight of at least about 30,000 daltons, more usually at least about 40,000 daltons, and may be as high as 60,000 or more daltons usually not exceeding about 300,000 daltons. The biliproteins will normally be comprised of from 2 to 3 different subunits, where the subunits may range from about 10,000 to about 60,000 molecular weight. The biliproteins are normally employed as obtained in their natural form from a wide variety of algae and cyanobacteria.

The presence of the protein in the biliproteins provides a wide range of functional groups for conjugation to proteinaceous and non-proteinaceous molecules. Functional groups that are present include amino, thiol, and carboxyl. In some instances, it may be desirable to introduce functional groups, particularly thiol groups when the biliprotein is to be conjugated to another protein. Each phycobiliprotein molecule contains a large number of chromophores. An exemplary ligand, e.g., an antibody molecule directly labeled with fluorescein will have between 1 and 3 chromophores associated with it. An antibody molecule (for example) directly labeled by conjugation with a phycobiliprotein may have as many as 34 associated chromophores, each with an absorbance and quantum yield roughly comparable to those of fluorescein.

Examples of phycobiliproteins useful in the present invention are phycocyanin, allophycocyanin (APC), allophycocyanin B, phycoerythrin (PE) and preferably R-phycoerythrin. PE is among the brightest fluorescent dyes currently available. Conjugated to an antibody, PE has been used to detect interleukin-4 in a fluorescent plate assay and found to be the only tested fluorophore that produced adequate signal (M. C. Custer and M. T. Lotze, 1990 *J. Immunol. Methods,* 128, 109–117).

The tandem dyes are non-naturally occurring molecules that may be formed of a phycobiliprotein and another dye. See, for example, U.S. Pat. Nos. 4,542,104 and 5,272,257. Examples of tandem dyes useful in the present invention are phycoerythrocyanin or PC5 (PE-Cy5, phycoerythrin-cyanin 5.1; excitation, 486–580 nm, emission, 660–680 nm) [A. S. Waggoner et al, 1993 *Ann. N.Y. Acad Sci.,* 677:185–193 and U.S. Pat. No. 5,171,846] and ECD (phycoerythrin-texas red; excitation, 486–575 nm, emission, 610–635 nm) [U.S. Pat. Nos. 4,542,104 and 5,272,257. Other known tandem dyes are PE-Cy7, APC-Cy5, and APC-Cy7 [M. Roederer et al, 1996 *Cytometry,* 24:191–197]. Tandem dyes, PC5 and ECD, have been successfully directly conjugated to monoclonal antibodies by several methods that involve iminothiolane activation of the dye.

Still other markers that may be directly conjugated to a ligand and used with the phycobiliproteins or tandem dyes in this invention to add additional numbers of markers (labeled ligands) to the method include small molecules that upon excitation emit wavelengths of less than 550 nm. Such molecules do not overlap with the emissions of the phycobiliproteins. One example of such a marker is fluorescein isothiocyanate (FITC). Others are listed in the Handbook cited above.

Still other markers that may be employed in this method to provide additional colors are the proteins known as the green fluorescent proteins and blue fluorescent proteins; also useful may be markers that emit upon excitation by ultraviolet light.

In another embodiment such markers may preferably be reporter genes, that upon expression produce detectable gene products. Such reporter sequences include without limitation, DNA sequences encoding a lux gene, beta-lactamase, a galactosidase enzyme, e.g., beta-galactosidase (LacZ), alkaline phosphatase, thymidine kinase, green fluorescent protein (GFP), chloramphenicol acetyltransferase (CAT), a luciferase enzyme, or a gluconase enzyme.

Still other suitable marker that may be attached to the ligands include membrane bound proteins including, for example, CD2, CD4, CD8, the influenza hemagglutinin protein, a biotin molecule and others well known in the art, to which high affinity antibodies directed thereto exist or can be produced by conventional means. Another class of markers includes fusion proteins comprising a membrane bound protein appropriately fused to an antigen tag domain from, among others, hemagglutinin or a Myc gene. Still other detectable labels may include hybridization or PCR probes.

Any number of additional, and conventionally employed, marker systems may be adapted to the method of this invention. One of skill understands that selection and/or implementation of a label system involves only routine experimentation. The biliproteins and tandem dyes are commercially available from various sources including Coulter International Corporation, Miami, Fla., Molecular Probes, Inc., Eugene, Oreg. and Prozyme, Inc., San Leandro, Calif. The other markers discussed above may be obtained commercially from known sources.

B. Methods of the Invention

The method of assessing pentraxin-binding of particles as discussed herein is useful for the diagnosis of a variety of diseases or abnormalities in mammals, particularly humans, in which the level of pentraxin binding on selected particles is altered from that of a normal sample. This method may be performed manually. Alternatively, the method may be implemented by a computer program.

The method involves exposing a biological test sample containing particles that comprise a pentraxin-binding moiety, e.g., a pentraxin-binding receptor from a test subject to a ligand comprising a pentraxin in the presence of calcium. The pentraxin ligand is preferably associated with a detectable marker. Conventional techniques may be utilized for construction of the pentraxin ligand-marker molecule. For example, the pentraxin ligand may be isolated from naturally occurring sources, or prepared synthetically by recombinant or chemical synthesis methods. Techniques of mutagenesis may also be used to modify a naturally occurring pentraxin. For example, these ligands may be prepared conventionally by resort to known chemical synthesis techniques, e.g., solid-phase chemical synthesis, such as described by Merrifield, 1963 *J. Amer. Chem. Soc.,* 85:2149–2154, and J. Stuart and J. Young, Solid Phase Peptide Synthesis, Pierce Chemical Company, Rockford, Ill. (1984). Alternatively, the ligands of this invention may be prepared by known recombinant DNA techniques and genetic engineering techniques, such as polymerase chain reaction, by cloning within a host microorganism, etc. (See, e.g., Sambrook et al., cited above; Ausubel et al. (1997), Current Protocols in Molecular Biology, John Wiley & Sons, New York). A selected pentraxin sequence and preferred marker sequence may be obtained from commercial sources (e.g., Invitrogen) or from gene banks derived from whole genomic DNA. These sequences, fragments thereof, modifications thereto and the full-length sequences are preferably constructed recombinantly using conventional molecular biology techniques, site-directed mutagenesis, genetic engineering or PCR, and the like by utilizing the information provided herein. For example, methods for producing the ligands or modifying them include mutagenesis of certain nucleotides and/or insertion or deletion of nucleotides are known and may be selected by one of skill in the art.

The preparation or synthesis of the ligand and/or marker sequences, whether in vitro or in vivo (including ex vivo) is well within the ability of the person having ordinary skill in the art using available material. The synthetic methods are not a limitation of this invention. The examples below detail presently preferred embodiments of synthesis of these molecules. The labels are coupled or fused to the pentraxin sequence by conventional means, suitable for the particular label. See, generally, Sambrook et al, cited above.

Once the desired recombinant molecules are engineered, they may be transferred to a selected mammalian cell for production purposes. Such methods include, for example, transfection, electroporation, liposome delivery, membrane fusion techniques, high velocity DNA-coated pellets, infection and protoplast fusion. Suitable mammalian cells include, without limitation, epithelial cells, endothelial cells, ganglion, lymphocytes, preferably B lymphocytes, monocytes. Examples of such cells include CHO, BHK, MDCK, and various murine cells, e.g., 10T1/2 and WEHI cells, African green monkey cells, suitable primate cells, e.g., VERO, COS1, COS7, BSC1, BSC 40, and BMT 10, and human cells such as WI38, MRC5, A549, human embryonic retinoblast (HER), human embryonic kidney (HEK), human embryonic lung (HEL), TH1080 cells. Other suitable cells may include NIH3T3 cells (subline of 3T3 cells), HepG2 cells (human liver carcinoma cell line), Saos-2 cells (human osteogenic sarcomas cell line), HuH7 cells or HeLa cells (human carcinoma cell line). Neither the selection of the mammalian species providing the host cells nor the type of cell is a limitation of this invention.

This exposure step can occur by adding to a sample in any typical laboratory equipment, e.g., a multi-well plate, an amount of ligand that is in excess of the anticipated or calculated number of pentraxin binding moieties on the particles in the sample. Alternatively, the particles in the sample may be immobilized prior to exposure to the ligand. Preferably, the ligand is suspended in a buffer containing from about 0.5 mM to about 5 mM of calcium. The calcium may also be present in the same concentration in any buffer that is used for washing or resuspending the cells. The total volume for each well used in the method of the invention comprises generally the test sample and the amount of excess ligand (including any amount of solvent contained therein) added. The total volume of sample and ligand is generally present in a standard dilution or ratio. Generally the ratio of the ligand to sample particles in the sample is limited only by the identity and amount of the solvent, if any, in which the ligand is present and upon the concentration of the particles in the sample.

Generally, the excess ligand is used at a concentration ranging from about 0.1 $\mu$M to about 50 $\mu$M, although higher and lower concentrations may be employed. Other concentrations may be used depending upon the concentration of the particles in the sample. The temperatures during these method steps are generally temperatures normal for the specified sample, and may be readily selected based on the known requirements of the selected sample and assay format. Preferably, during the course of the method, the sample is incubated in a controlled humidity before and after contact with the ligand. The humidity of the incubation is controlled to minimize evaporation from the microtiter vessel, and permit the use of small volumes. Alternatively, or in addition to controlling humidity, the vessels may be covered with lids in order to minimize evaporation. Selection of the incubation temperature depends upon the identity of the sample, primarily. Selection of the percent humidity to control evaporation is based upon the selected volume of the vessel and concentration and volume of the ligand and sample in the vessel, as well as upon the incubation temperature. Thus, the humidity may vary from about 10% to about 80%. It should be understood that selection of a suitable incubation temperature, and time of incubation and selection of controlled humidity is well within the skill of the art. See the texts cited immediately above.

The exposure occurs for a time sufficient for the pentraxin ligand to bind any available pentraxin-binding moieties on the particles. Generally, such a time may range from 15 minutes to overnight, i.e., about 8 hours. Preferably, the pentraxin ligand is associated with a detectable marker, such as those described specifically above.

After sufficient time for the binding to occur, the particles now carrying bound ligand are optionally separated from the excess unbound ligand by a conventional method, such as by rinsing, gentle extraction through a separation column, centrifugation, magnetic beads. The determining step comprises detecting the presence or expression of marker that corresponds to the level of binding between ligand and particle. This quantitative evaluation can be reported as the percentage of particles bound to said ligand or the amount or number or amount of ligand bound per particle. The detecting method utilized must be compatible with the nature of the marker itself. The means of marker or signal detection depend upon the identity of the marker attached to the pentraxin ligand and/or other ligand bound to the particles in the sample. Such means of detection include, without limitation, enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

For example, where the marker is beta-galactosidase, assays for beta-galactosidase activity are used to detect expression of the label. Where the selected label is luciferase, its expression by the synthetic sequence of the present invention may be detected by light production in a luminometer. In another example, each test sample (as well as any control that contains a known amount or number of particles with a known number and amount of pentraxin-binding moieties) is analyzed on an instrument that measures a signal generated by the selected marker. In some embodiments, the binding is measured directly, by detecting the amount of ligand associated with a directly detectable marker, e.g., a luminescent marker. In other embodiments the binding is measured indirectly, e.g., where the ligand is associated with a protein, e.g., biotin, and where the marker is associated with the anti-biotin molecule, avidin. In this circumstance, after the biotin-labeled ligand is introduced into the sample and excess ligand removed from the sample, the substrate binding protein, avidin associated with a marker is introduced. When excess avidin is removed, the marker is then measured.

The measurement of the quantity of particle-bound ligand can be made using an instrument that detects whatever signal is generated by the marker or marker/substrate combination, e.g., luminescence, or that detects signals from direct current, radio frequency current, light scatter, fluorescence, and combinations thereof. Only ligands that have bound via the pentraxin-binding moiety or receptor on the surface of the particle are detected by these marker systems. Unlabeled receptors on the particles and soluble labeled ligand or labeled substrate are not measured. Most preferably, the instrument measures light scatter and fluorescent emission of particles to which are attached bound labeled ligands. For example, the excitation radiation from a flow cytometer causes the markers on the labeled ligands to produce a signal detectable as mean channel intensity of the fluorescence (or enhanced Raman intensity) or light scatter. Only the labeled ligands bound to receptors on the particles are detected in this manner. Any unbound labeled ligand in the sample is not measured by the flow cytometer. Thus, for each set of control samples and test samples, a mean channel intensity value for each concentration of labeled ligand in the sample is obtained. The mean fluorescent intensities preferably span the range of receptor occupancy from about $\frac{1}{100}$ to about 100% of saturation (saturation being defined as all receptors sites filled by labeled ligand).

With regard to the detection of the binding level, more than a single detection or type of detection may be employed to detect the signal(s) of the marker(s) on the pentraxin ligand and/or any other additional ligand employed in this method. The detecting steps may be repeated for multiple different ligands in the same sample, or repeated for the same ligand on multiple different samples. The method may repeat the same or different detecting steps for multiple different ligands on the same sample. Alternatively the method may include repeating the same or different detecting steps for the same ligands on multiple different samples or particles.

Once the level of binding between ligand and pentraxin-binding moiety on the particles is determined, that level in the test sample is compared to the level of binding in a control biological sample containing said particles from a healthy subject of the same species as the subject supplying the test sample. Alternatively, if normal levels of pentraxin-binding moieties on certain particles are known, the test sample level may be compared with known "normal" levels available in conventional diagnostic charts. A significant change in the level of binding in said test sample from that of the control is indicative of disease or abnormality.

In the examples below, the pentraxin exemplified is human CRP, the sample is human peripheral blood and the particles are monocytes. As described in more detail below, an increase in the percentage of CRP-bound monocytes or the number of CRP molecules bound per cell, in a test sample of human peripheral blood over the same percentage or number in a control is indicative of an auto-immune disorder or other immune disorder. Among the immune disorders or auto-immune disorders that exhibit significant increases or decreases of CRP binding to monocytes are included, without limitation, diabetes, multiple sclerosis, Sjorgen's Syndrome rheumatoid arthritis, and systemic lupus erythematosis. Still other such disorders may exhibit such aberrant CRP or other pentraxin binding by hematological cells, when biological samples of patients with these disorders are evaluated according to the methods description herein.

Additionally, a decrease in the percentage of CRP-bound hematological cells or the number of CRP molecules bound per hematological cell, in a test sample of mammalian body fluid over the said same percentage or number in a normal healthy control is indicative of an inflammatory disorder, sepsis or cancer. A decrease in the percentage of CRP-bound hematological cells or the number of CRP molecules bound per cell, in a test sample of blood from a mammalian patient over the same percentage or number in a control is indicative of cancer.

In a mammal bearing symptoms of infection, the method of this invention may be used to distinguish between bacterial and viral, or other parasitic infection. The appearance of a distinct cluster of CRP-bound cells in a light scatter region equivalent to that of lymphocytes in a test sample of infected mammalian blood over the same percentage in an uninfected control is indicative of the presence of a bacterial infection. Among such bacteria that cause this decrease are included, without limitation, *S. pneumoniae, P. aeruginosa* and *T. galbrata*, among many other known bacteria.

Another embodiment of this method includes the step of introducing to the sample, preferably before, the determining step, a second or further additional non-pentraxin ligand (s) that binds non-pentraxin receptors on the selected particles. For example, ligands that are known to bind to a selected particle, such as a hematological cell, may be added to the test sample to aid in the further analysis of the sample. In one example, ligands for other known receptors on monocytes may be added to a sample of peripheral blood when CRP is the pentraxin ligand. Such additional ligands may include ligands referred to as CD64, CD14, CD16, CD45RA, CD33, CD142 and HLA-DR ligands. Each additional ligand may be associated with a marker that is different from that associated with the pentraxin ligand, if desirable. The determining step in this embodiment of the method further includes determining the amount or percentage of binding between the additional ligand and its known receptor on the cell. This information enables one of skill in the art to further evaluate the condition of the patient test sample. The level of additional ligand binding and any aberrance in this level from levels normal for a healthy control species may be a factor that is also introduced and relevant to proper diagnosis or disease or abnormality.

In still another embodiment and advantage of the method of this invention, the above-described method may be implemented by a computer program. A computer program is provided that performs the analysis and calculations described above. More specifically, the computer program is designed to record, sort and calculate the parameters of the method provided above, including the mean channel values, the molar concentrations of the ligands, and to obtain the necessary analytical results. In a preferred embodiment, this computer program is integrated into the particle analysis instrument, particularly a hematology instrument or flow-cytometer. In still other embodiments, the program is on a separate computer that is a "plug-in" device for attachment to the analysis instrument. Still another embodiment of this invention is a computer program that is present on a standalone computer, into which data from the instrument is fed. Alternatively, the method of this invention can be generated by use of conventional spreadsheet programs on standalone personal computers.

This computer program comprises means for translating data as to the marker detection recorded by the particle analysis instrument, e.g., by measuring a range of mean channel fluorescence intensity numbers or other signals generated by the marker, and measuring the concentrations or titers of pentraxin-ligand and additional non-pentraxin ligand populations in test samples. The program preferably performs all of the calculations necessary to perform the method of this invention by analyzing the data on the test samples or control containing particles, and/or receptors. In still another embodiment of this program, it can provide an electrical signal or warning when an aberrant result, e.g., a significant increase or decrease of pentraxin binding, or a combination of aberrant results from the pentraxin ligand binding and/or the additional ligand binding, is identified.

In still another embodiment of this invention, an analysis instrument, e.g., a flow cytometer, is provided that comprises an integrated computer program that identifies and analyzes the amount of receptor on the surface of a particle in a biological sample comprising particles by implementing the program and method steps described above.

C. A Diagnostic Kit of This Invention.

In yet another aspect of this invention, a diagnostic kit is provided for assessing the level of pentraxin-binding moieties on particles in a biological sample that are associated with disease states. In one embodiment, the kit contains a ligand comprising at least one pentraxin, as described above. In some embodiments, more than one pentraxin ligand may be desired. The kit may also contain one or more additional ligand that binds to a moiety on the particles that is not pentraxin-binding. Further components of the kit would include one or more detectable markers for labeling the pentraxin ligand and/or the additional ligand by methods described above. Preferably at least two different markers or marker systems are provided, to enable differential labeling of the pentraxin ligand and the additional ligand(s).

For performance of the method of this invention, the kit also contains a buffer solution containing calcium at a concentration of between about 0.5 and 5 mM calcium for use in suspending the ligand, or washing or resuspending the cells in the performance of a calcium-dependent cell-based assay for the selected disease.

Other components of this method are readily adaptable into a kit that contains one or more ligands, both labeled and unlabeled or one or more detectable markers for labeling a suitable ligand, suitable vessels for containing samples, and suitable controls or tables of normal values of ligand-particle binding. The kit of the present invention can contain either the same or different detector markers, whereby a plurality of samples can be examined with the same particle analysis instruments. These kits can additionally contain reagents necessary to maintain or preserve the biological samples.

More importantly, the kit contains instructions for performing the method suitable to the particular immune disorder, abnormality or bacterial infection being diagnosed, and for preparing the controls. Also provided in a kit may be suitable diluents and buffers for the samples, indicator charts for signal comparisons, disposable gloves, decontamination instructions, applicator sticks or containers, and sample preparator cups. The kits preferably also contain necessary buffer substances or media, as required. One of skill in the art could assemble any number of kits with the information and components necessary to perform the method on a patient for any specific disorder in which pentraxin-binding receptors are present on selected cells at a significant increase or decrease compared to a normal, healthy sample, and compare the results to norms for that receptor.

D. Examples of This Invention

The following examples demonstrate the methods, kits and components of the present invention, and demonstrate use in analyzing and enumerating the pentraxin-binding receptor variations in normal humans and those with a disease. Utilizing a flow cytometric ligand binding assay, a monocyte population in human peripheral blood and specific human-derived myelomonocytic cell lines was demonstrated to reproducibly bind a conformational pentraxin epitope on human CRP through a mechanism that does not involve its ligand, phosphorylcholine. The recognition site on these cells is not unique to human CRP, but is directed to a calcium induced native conformation, that may be an evolutionarily conserved pentraxin epitope.

These examples also demonstrate an evaluation of 81 healthy donors using a flow cytometric assay with a pentraxin ligand, which showed that a majority of peripheral blood monocytes (67.9±1.3, mean±sem) bound CRP. The percentage of binding was normally distributed and not affected by gender, age or ethnicity. The assay of this invention was then performed on samples of whole blood obtained from donors representing a variety of disease states. The results showed a significant reduction in the level of CRP bound by monocytes in those donors classified with infection, inflammation or cancer. This reduction in monocyte populations binding CRP did not correlate with the concentration of plasma CRP.

The following examples illustrate various aspects of this invention. These examples do not limit the scope of this invention that is defined by the appended claims.

EXAMPLE 1

Antibodies

The monoclonal antibodies (MAb), and isotypic antibodies used in the following experiments were obtained from Coulter Corporation, Miami, Fla. The MAbs include, without limitation, CD4 (T lymphocytes and monocytes of peripheral blood); CD8 (T lymphocytes and some NK cells); CD11a (lymphocytes, granulocytes and monocytes); CD11b (myeloid and NK cells); CD11c (myeloid cells, NK cells and activated T cells); CD13 (monocytes, granulocytes and their precursors); CD14 (monocytes, with low levels on granulocytes and B cells); CD15 (neutrophils, eosinophils and monocytes); (neutrophils, NK cells); CD19 (B cells); CD29 (all leucocytes); CD32 (granulocytes, monocytes, B cells and platelets); CD33 (monocytes); CD36 (platelets and monocytes); CD45RA (T cell subsets, B cells, and activated monocytes); CD45RO (T cell subsets, monocytes and granulocytes); CD49d (most leukocytes except neutrophils); CD54 (monocytes, activated T and B cells); CD56 (NK cells, T cell subsets); CD64 (monocytes; may be induced on neutrophils by IFNγ); HLA-DR (B cells, monocytes and activated T cells); and MPO (expressed on myeloperoxidase, an intracellular enzyme contained in the azurophilic granules of neutrophils).

Monoclonal antibodies conjugated to fluorescein isothiocyanate (FITC), were used for staining the cell lines (KG1a, U937, THP-1 and HL60). Phycoerythrin (PE) or phycoerythrin-cyanine 5.1 (PC5) conjugated MAbs were used in two and three color combinations with bCRP:dichlorotriazinyl amino fluorescein conjugated—streptavidin (SA-DTAF) (Coulter Corporation, Miami, Fla.) for the staining of peripheral whole blood.

Corresponding fluorochrome conjugated mouse monoclonal isotypic antibodies IgG1, IgG2a and IgM were used as negative controls to determine cursor placement for percent positive values or for establishing Relative Fluorescence Intensity (RFI) to a negative peak. The median fluorescent peak (MdX) encompassing the peak of the positively stained population was read directly from the histogram.

EXAMPLE 2

Staining Conditions for Flow Cytometry

A. Cell Lines

The optimal, saturating, concentration of bCRP on cell lines was determined by titration of 100 $\mu$L bCRP containing 50 $\mu$g/mL phosphorylcholine (PC; Sigma, St. Louis, Mo.) with 100 $\mu$L THP-1 cells ($1\times10^6$ cells) in triplicate using the corresponding concentration of bHSA with PC as a negative staining control. After 30 minutes on ice the exposed cells were either washed with 3 mL cold HFCS, centrifuged at 500×g for 3 minutes and resuspended in 100 $\mu$L cold HSFC, or left alone to compare washed and non-washed systems. Freshly diluted SA-DTAF in HSFC, 100 $\mu$L (9 $\mu$g SA-DTAF), was then added to the tubes and incubation proceeded for another 15 minutes on ice protected from light. The stained cells were washed using 3 mL cold HSFC, centrifuged at 500×g for 3 minutes and resuspended in 1 mL cold HSFC containing 0.3% paraformaldehyde (Sigma). Flow cytometric analysis was performed immediately.

Once the optimal concentration of bCRP for each system (wash vs. no wash) was selected, the primary incubation time (15 to 45 minutes) was determined. The concentration of bCRP and incubation time selected was then used for all other experiments. The labeling reagent, SA-DTAF, was kept at a constant 1:200 dilution. For staining of selected cell lines with antibodies, 20 µL antibody was added to 100 µL cells (1×10$^6$ cells) and incubated, covered, at room temperature for 20 minutes. The cells were then washed with 3 mL HSFC and resuspended to 1 mL containing 0.3% paraformaldehyde. Intracellular myeloperoxidase (MPO) staining of cells was accomplished by treating the cells with IntraPrep Permeabilization Reagent (Coulter Corporation) 1 for 15 minutes at room temperature. The cells were then washed with 4 mL PBS, treated with IntraPrep Permeabilization Reagent 2 for 5 minutes and stained with MsIgG2a-FITC or MPO-FITC for 15 minutes at room temperature. After the second incubation was completed, the cells were washed with 4 mL PBS, and resuspended as described above for antibody staining.

B. Peripheral Blood

Normal peripheral blood and second sample peripheral blood samples were drawn into EDTA containing tubes, unless noted, and stored at room temperature. Blood was stained within 10 hours of collection. To evaluate binding of bCRP in peripheral whole blood without any potential interference from plasma CRP, the red cells were lysed prior to staining. This eliminated an extra lyse/wash step at the end of the assay, minimized the loss of monocytes and simultaneously removed any plasma or bound CRP from the cell surface. In addition the removal of the plasma and red cells allowed calcium to be incorporated into the buffer system without subsequent clotting. Lysis was accomplished either by adding a volume of 3 mL of ammonium chloride (Sigma) containing EDTA (Sigma) solution to each 100 µL whole blood for 10 minutes at room temperature or by using the automated T-QPrep Workstation with the ImmunoPrep Reagent System (Coulter Corporation). The ImmunoPrep Reagent System consists of an acid lyse, followed by neutralization and fixation. The lysed blood was centrifuged, the supernatant decanted and the remaining white cell pellet resuspended in 100 µL 0.01M HEPES (Sigma)—0.15M sodium chloride containing 2% Fetal Calf Serum and 2 mM calcium chloride (Sigma), pH 7.4 (HSFC). A volume of 100 µL of bCRP, or the bHSA control, was then added to the lysed whole blood (~1×10$^5$ cells) and the mixture was kept on ice for 15 minutes. At the end of this time SA-DTAF at a 1:500 dilution (3.6 µg) and 10–20 µL of the appropriate antibody or isotype combination was added for an additional 15 minutes on ice. Cells were then washed with 3 mL HSFC, centrifuged and resuspended to 1 mL in HSFC (0.3% paraformaldehyde was added to ammonium chloride-lysed cells). Stained cells were kept on ice and analyzed within the hour.

The optimal, saturating, concentration of bCRP in peripheral blood was determined by titration of 100 µL bCRP with 100 µL cells (~1×10$^5$ cells) on four different donors on two separate days using the corresponding concentration of bHSA as a negative staining control. This concentration was used for all subsequent staining. Freshly drawn blood was evaluated within 30 to 60 minutes of collection and examined with specific markers identifying cell populations to ensure that the receptor binding pattern was similar to that obtained up to 10 hours later.

The binding occurred in both washed and unwashed systems, substantiating that the reaction was not an artifact of non-specific binding that may have occurred in prior non-washed systems. The improvement in this assay over than of Ballou et al, may be due to the quality of the reagents, the use of HEPES in place of HBSS, the additional FCS, reduced manipulation of the peripheral blood or the use of a longer spacer arm for the biotinylation.

EXAMPLE 3

Flow Cytometric Analysis

A. Quality Control

Quality control and set up of the flow cytometer (EPICS XL-MCL, Coulter Corporation, Miami, Fla.) consisted of alignment and fluidics verification using Flow-Chek fluorospheres (Coulter Corporation) and the standardization of light scatter and fluorescence intensity with Flow-Set fluorospheres (Coulter Corporation). Negative staining controls consisted of the corresponding fluorochrome-conjugated mouse monoclonal isotypes and the bHSA:SA-DTAF. CRP was biotinylated according to the manufacturer's instructions (Biotin-X-NHS kit, Calbiochem-Novabiochem; LaJolla, Calif. and stored, if necessary, at 4° C. Purity and yield of this conjugated ligand was determined by radial immunodiffusion (RID) and crossed immunoelectrophoresis (XEP), and SDS-PAGE, all performed conventionally.

B. Cell Lines

Target mean channels previously determined for cell lines stained with mouse IgG1-FITC were used to maintain consistency of values. The same fluorescent settings for FITC emission (LFL1) were used for all cell lines to enable direct comparison of median fluorescent intensities. Forward and side light scatter settings were adjusted to accommodate the differences between the cell lines for these parameters. Due to differences in scatter and fluorescent uptake, separate settings were established for MPO. Since cell lines consist of a relatively uniform population of cells, a Relative Fluorescent Index (RFI) comparing the level of fluorescence to the negative control was used as a more accurate representation of binding levels. The median value for the peak fluorescence (MdX) was used in place of the mean fluorescence intensity so that any skewed population shifts would be captured.

C. Peripheral Blood

After collection into EDTA containing tubes, and storage at room temperature, blood samples were evaluated on a Coulter STKS hematology analyzer as a routine initial screen. On occasion after whole blood was used for flow cytometry, the remaining blood was centrifuged to remove the separated plasma. The plasma was placed in a cryotube and sodium azide was then added to obtain a final concentration of 0.1%. Plasma samples were stored at 4 C and used for quantitation of the plasma CRP concentration.

Voltage and gain settings for FITC (DTAF), PE and PC5 stained whole blood were determined using the appropriate single color negative or isotypic controls. Color compensation was adjusted using CD4-FITC+CD8-PE stained cells for the 2 color setup followed by compensation of CD4-PE+CD8-PC5 stained cells for the 3 color setup. Verification of the correct settings for 3 color analysis was confirmed with triCHROME CD8-FITC/CD4-PE/CD3-PC5 stained cells.

Three-color panels, selected to identify specific cell populations, were set up as follows:

bHSA:SA-DTAF/IgG1-PE, or IgG2a-PE/IgG1-PC5 (negative control)

bCRP:SA-DTAF/CDT-PE+CD8-PE/CD13-PC5 (T cells, myeloid cells)

bCRP:SA-DTAF/CD19-PE/CD33-PC5 (B cells, myeloid cells)

bCRP:SA-DTAF/CD56-PE/CD16-PC5 (NK cells, neutrophils)

bCRP:SA-DTAF/CD14-PE/CD16-PC5 (monocytes, neutrophils)

Other three-color panels used routinely were:

bCRP:SA-DTAF/IgG1-PE, or IgG2a-PE/IgG1-PC5 (isotype control)

bCRP:SA-DTAF/CD64-PE/CD13-PC5 (monocytes, myeloid cells)

bCRP:SA-DTAF/HLA-DR-PE/CD33-PC5 (MHC-bearing cells, nyeloid cells)

Two color panels consisted of the bHSA:SA-DTAF with IgG1-PE, IgG2a-PE or the MAb-PE and the corresponding tubes containing bCRP:SA-DTAF. To ensure that enough monocytes were collected for the analysis stop counts were set to collect at least 1000 monocyte events based on forward and side scatter parameters.

D. Software and Statistical Analyses

For analysis of flow cytometry results System II version 3 software (Coulter. Miami, Fla.) or WinMDI version 2.8 (J. Trotter, Scripps Research Inst., LaJolla, Calif.) were used. Determination of means and standard errors were calculated using Microsoft Excel 97 (Microsoft, Redmond, Wash.). All other statistical analysis (Pearson correlation, K-Means Cluster, e.g.) utilized SPSS Base 9.0 (SPSS, Inc., Chicago, Ill.).

EXAMPLE 4

Multiparameter Flow Cytometric Analysis of CRP Binding to Human-Derived Cell Lines Utilizing a Functional Ligand Binding Assay Human leukemia-lymphoma cell lines that are monoclonal in origin and represent various stages of differentiation were used to examine the binding of CRP to the various cells. The following cell lines were obtained originally from the ATCC (Rockville, Md.) and were maintained in RPMI-1640 media or McCoys media supplemented with 1% L-glutamine, 1% Penicillin/Streptamicin and containing 10% heat inactivated fetal calf serum. The cell lines included HL-60, characterized as promyelocytic; THP-1, a monocytic line; U937, considered to be monoblastic; KG-1a, undifferentiated blast cells; Raji, the first human lymphoma cell line established; Daudi, an Epstein Barr Virus transformed lymphoma and MOLT-4, derived from a T cell leukemia. The HL-60 cell line also represents cells that are at the crossroads of myelocyte vs. monocyte differentiation. The ability to induce one path or the other has been utilized to demonstrate the up-regulation or down-regulation of numerous cell surface markers, mRNA or cytoplasmic. These cells provided a convenient method to test CRP binding to monocytes and/or myelocytes.

The human Leukocyte Differentiation Antigens (HLDA) clustered monoclonal antibodies to known surface antigens and to the cytoplasmic enzyme, MPO, identified in Example 1 above, were used to further define and confirm the accepted cell-differentiation stage as well as to characterize, or fingerprint, the cell lines used.

HL-60 was induced towards either the granulocyte or monocyte pathway with DMSO or phorbol-12-myristate-13-acetate (PMA), respectively. To induce the myelocyte differentiation pathway of HL-60 cells into mature myelocytes or monocytes, a concentration of 1.2% DMSO (Baxter Research, Midvale, Utah) included in the media was added to $2.5 \times 10^5$ cells/mL for 6 to 14 days. Monocyte differentiation of HL60 cells was promoted by exposing $5 \times 10^5$ cells/mL to 16 nM PMA for 48–72 hours prior to harvest. Untreated cells were always harvested along with the treated cells on the day of testing. A control using the same concentration of PMA dissolution media (DMSO) was also monitored. Viability of cells was determined by trypan blue exclusion and was always greater than 95% except for PMA treated cells that consistently were at 84% due to removal of the adherent cells from the flask via scraping. Prior to staining, the cells were washed with 10 mM HEPES, 150 mM sodium chloride buffer, pH 7.4 containing 0.01% sodium azide, 2% heat-inactivated fetal calf serum and 2 mM calcium chloride (HSFC) and resuspended to $1 \times 10^7$ cells/mL.

The concentration of bCRP necessary for saturation was determined by titration of the bCRP and bHSA as serial two-fold dilutions from 1:25 to 1:800 for the non-washed assay and from 1:5 to 1:1280 for the washed assay. The primary incubation time and the SA-DTAF dilution were kept constant for both types of assay. A dilution of bCRP between 1:50 and 1:100 for the non-washed assay, representing a concentration of less than 1 $\mu$g per $10^6$ cells, exhibited the highest percentage of positive cells with the RFI. The RFI was determined by dividing the fluorescent intensity, measured by the Median X (MdX) parameter, for each dilution of bCRP by the corresponding negative control, bHSA MdX. This parameter is more useful than percent positive in clonal populations where all cells will bind or not bind. For the washed assay, a bCRP concentration between 27 and 54 $\mu$g/mL appeared to be optimal on the THP-1 cell line. Both systems exhibited a 'prozone'-like effect at the highest concentrations that may be due to steric hindrance or quenching by closely spaced fluorescein molecules. Based on this experiment the concentration used for the washed assay was set at a dilution of 1:15 or approximately 36 $\mu$g/mL.

The time of incubation of the primary reaction with bCRP (15, 30 or 45 minutes) was compared for the wash and no wash assay systems keeping the concentration of bCRP at the predetermined optimal level and the SA-DTAF constant at a 1:200 dilution. Both assays gave the optimal RFI at 30 minutes and, though the wash assay clearly gives an improved signal at all time periods, the pattern of reactivity is similar.

A variety of cell lines at different stages of differentiation were examined. The cell line showing the highest binding characteristics was the monocytic cell line, THP-1 (RFI of 14.5 in the washed assay), followed by U937 (RFI of 1.3 in the washed assay) and KG-1a (RFI of 1.2 in the washed assay) cells in either system. The HL-60 cell line was induced towards either the granulocyte or monocyte pathway with DMSO or PMA, respectively. Binding to untreated or DMSO-treated HL-60 cells, was negative in both the washed and no-wash systems. Binding to the T cell and B-cell derived lines, (Raji, Daudi and MOLT-4) was negligible in both the washed (all RFI under 0.9) and no-wash systems.

HL-60 cells treated with PMA showed increased binding of CRP, similar to U-937 cells. The RFI for PMA-72 was 1.5, for PMA-48, 1.2; for CTL 0.7; for DMSO, 1.0; for HL60, 0.6 and for THP-1, 25.1. THP-1 cells were run at the same time as a positive control along with untreated HL-60 cells and HL-60 cells that were used as a control for PMA-treated cells (treated to the same dilution of DMSO that the PMA had been dissolved in). Increases in CD11b, CD13, CD15, CD16, CD33, CD49d and MPO along with observable morphological changes associated with granulocytes occurred on DMSO-treated HL-60 cells. Dramatic increases of CD11b, CD13, CD36 and CD54 were observed in the PMA-treated cells along with significantly decreased expression of CD4, CD15, CD33, CD49d and MPO, similar to previous reports. PMA-treated cells also exhibited the expected adherent properties and morphology of monocyte differentiation.

No obvious correlation with bCRP binding was seen with the expression or depression of any of the surface markers (CD4, CD11b, CD13, CD14, CD15, CD16, CD33, CD36, CD49d, CD54, HLA-DR and MPO) in the myelomonocytic cell lines examined. Optimal binding in the non-washed system in THP-1 cells occurred above 1.25 mM calcium Incubation with half of the calcium also resulted in observably lower binding of bCRP to the THP-1 cells. In the washed assay, binding of bCRP was abolished with the incorporation of 5 mM EDTA in the primary incubation, while PC inclusion or exclusion from the reaction mixture showed no significant difference.

The relative expression of CD14 (LPSR) was inconclusive due to the higher nonspecific binding of the IgG2a-FITC isotypic control. CD64 (FcγRI), which has previously been implicated as the receptor or co-receptor showed a high expression on THP-1 cells, followed closely by U937 and HL-60 but was not expressed on KG-1a cells.

The direct demonstration of the binding of bCRP to PMA-treated HL-60 cells and the minimal binding seen with either untreated or DMSO-treated cells refutes previously-reported findings and indicates that cells that bind CRP are more committed to monocyte differentiation. The patterns of expression of markers on the treated HL-60 cells as well as adherence and morphology were similar to previous reports and confirmed the monocyte and myelocyte differentiation. The additional evidence of binding to U-937 and especially THP-1 cell lines further defines the expression of this binding moiety to be on early monocytic cells. The binding to KG-1a cells indicates that binding of CRP may occur on very early myeloid cells since this line was derived from an acute myelogenous leukemia. A novel observation was that the THP-1 and the KG-1a cell lines bind CRP. In fact the THP-1 line showed the most dramatic and avid binding of all the cell lines examined and makes this an excellent model to use in the isolation of the receptor. The inclusion of cell lines representative of B and T cells confirmed the lack of expression on cells committed to the lymphoid pathway.

A reproducible method for analysis of CRP binding to cell lines has been demonstrated. This binding is saturable, requires calcium, and is not inhibited by phosphorylcholine or immunoglobulin. The binding occurs on cells of myelomonocytic origin. The increase in CRP binding on PMA induced HL60 cells but not on HL-60 or DMSO-treated HL-60 cells strongly implies that the receptor is expressed on monocytic and promonocytic cells rather than promyelocytes.

The binding moiety on the cell surface recognizes an epitope found on human CRP and SAP and Limulin CRP. The receptor is not 'specific' for human CRP but may be a pentraxin receptor indicating that the recognition site is a conserved region (possibly the pentraxin motif and calcium binding region). The binding site requires the calcium conformation of CRP for recognition.

EXAMPLE 5

Inhibition

To determine whether purified CRPs from human and horseshoe crab, CRP defined fragments of CRP amino acid residues 77–82, 174–185, and 201–206 of SEQ ID NO: 2 (Sigma, St. Louis, Mo.), and another pentraxin, human Serum Amyloid P (SAP), >99% purity (Sigma, St. Louis, Mo. or Calbiochem-Novabiochem, LaJolla, Calif.), had an inhibitory effect on the binding of bCRP to THP-1 cells, varying amounts of these potential inhibitors were combined with an equal volume of bCRP. The bCRP was kept at a saturating concentration of approximately 1 μg/mL (100 ngs per reaction). Staining proceeded using the previously determined optimal non-washed conditions. Human Serum Albumin (HSA) >99% purity (Calbiochem-Novabiochem, LaJolla, Calif.) was added in a similar fashion to the other inhibitors and used as a control value from which to compare the results of the other inhibitors.

Purified human CRP inhibited the binding in a dose-dependent manner supporting the specificity of the assay. The point at which 50% of the binding was inhibited occurred at 0.72 μgs CRP ($6.3 \times 10^{-12}$ M) in the non-washed assay. Additional insight as to the nature of the reaction was demonstrated by inhibition with Limulus CRP, with 50% inhibition occurring at $8.7 \times 10^{-12}$ M, and, to a lesser extent, human SAP at $1.5 \times 10^{-10}$ M. The CRP fragment 174–185 of SEQ ID NO: 2 appeared to suppress the reaction at 100 μgs (~128 M solution) but was not repeated. The other fragments (up to 200 μgs) as well as the HSA showed no inhibition (fragments not shown).

Inhibition studies with Limulin and human SAP demonstrated that the binding site is a conserved pentraxin epitope. The calcium requirement necessary for binding to occur indicated that the cells recognize a conformational form of CRP. Phosphorylcholine did not inhibit the reaction, discounting the possibility that CRP had bound to damaged membranes with exposed PC sites.

The requirement for calcium in the binding of bCRP to THP-1 cells was evaluated by a series of buffers containing increasing concentrations of calcium along with the effects of 5 mM EDTA and 100 μgs phosphorylcholine (PC). A series of 0.01M HEPES-Saline2% FCS buffers were made with increasing concentrations of calcium added (0.5 mM to 8 mM) to bCRP kept at approximately 1 μg/nL. The addition of 5 mM EDTA to the HSFC buffer used to dilute bCRP was also examined. The effect of phosphorylcholine (PC) on the binding reaction was examined by excluding it from the HSFC buffer used to dilute bCRP. All other staining conditions were as previously described using bHSA as the control.

The specificity was re-confirmed on human peripheral blood at a single concentration of inhibitor. The inhibition experiments with purified human CRP demonstrated that, despite the charge/conformation changes due to biotinylation, the binding of bCRP was directed to a native CRP epitope that was not 'hidden'.

In contrast to prior reports, this experiment clearly demonstrates that calcium is required for optimal binding of CRP. The necessity for calcium implicates that the amino acid residues involved lie in the calcium binding region (residues 134–148 and/or 152–176 of SEQ ID NO:2) or are affected by calcium binding. This area may be in or near the loop structure held in place by calcium ligation. Though CRP fragment 174–185 of SEQ ID NO: 2, which borders one of the calcium regions, appeared to suppress the reaction at 100 μgs, the volume used to obtain this concentration was four times that of the bCRP reaction volume and the inhibition seen may have been a dilution effect.

Based on the recently reported crystallographic structure of these pentraxins it is probable that the binding site for native CRP encompasses or is affected by the conformational changes at residues 134–148 of SEQ ID NO: 2 (calcium-binding region) which are highly conserved among the pentraxins. Since ligand binding does not occur without the conformational change due to calcium, CRP binding by the receptor in situ probably occurs more often with a CRP complex. In light of the many potential CRP complexes (snRNPs, chromatin, bacterial cell walls, etc.) this interaction suggests a mechanism for clearance of apoptotic and necrotic debris in addition to bacteria.

The necessity for calcium and the inhibition of the binding to THP-1 cells by human CRP, horseshoe crab CRP and human SAP point to a calcium-dependent conformational epitope that is evolutionarily conserved. It was previously unknown that limulin or human SAP can inhibit the binding of human CRP to peripheral blood monocytes or THP-1 cells. The inhibition studies demonstrate that the binding moiety appears to exhibit a lower affinity for SAP but this may be due to the propensity for SAP to aggregate in higher calcium environments and thus sterically hinder the site recognition. That the peripheral blood monocytes appeared to bind SAP better than the cell lines suggests a difference in binding affinity between cultured leukemia-derived cells and freshly drawn blood. Another possibility is that in humans, where CRP behaves as an acute phase protein and SAP is constitutively expressed at levels of 30–50 $\mu$g/mL, clearance of normal apoptotic debris is via the lower affinity binding to SAP. The higher affinity for CRP is necessary when its levels rise rapidly due to an inflammatory stimulus. Circulating monocytes that bind CRP may be an important factor in the clearance of CRP-complexes (snRNPs, CRP-anti-CRP).

No other reports of the CRP binding site have used other CRPs or pentraxins to successfully inhibit binding. This data along with the reported binding of human CRP to mouse macrophage cell lines suggests that the binding moiety itself is conserved. The acute-phase nature of the pentraxin is dependent upon the species: CRP in humans, SAP in mice and CRP/SAP hybrid in hamsters. The finding of SAP in amyloid fibrils of the brain and the possible association with Alzheimer's Disease also indicates that the acute-phase nature may be dependent upon the environment. A conserved receptor on a phagocytic cell, such as the monocyte/macrophage, that recognizes a conserved pentraxin epitope allows the organism the ability to bind whichever pentraxin is upregulated in that species or within the environment.

EXAMPLE 6

Multiparameter Flow Cytometric Analysis of CRP Binding to Normal Human Peripheral Blood Leukocytes Utilizing a Functional Ligand Binding Assay Human whole blood from 81 individual donors was used as a source of normally occurring peripheral blood cell populations. Samples were classified according to age, gender and ethnicity. Freshly drawn blood was evaluated to ensure that binding was not effected by the age of the blood.

Purified human CRP and HSA were labeled with biotin and detected with a streptavidin conjugated fluorescein derivative (DTAF) as previously described. The assay was optimized for use with human peripheral blood cells. ImmunoPrep reagent or ammonium chloride was used to lyse red cells and remove any plasma CRP prior to staining. This allowed all leukocyte cell populations to be examined without resorting to ficoll or other density gradient separation techniques that entail more manipulation of cells and extensive washing that could damage the cell membrane.

The specificity of the assay system was evaluated by the inhibition of the binding of biotin-labeled CRP (bCRP) by purified human CRP. Inhibition by phosphorylcholine (PC), human immunoglobulin G (hIgG), the human SAP and EDTA was also examined. Multiparametric flow cytometric assays employed a bCRP:SA-DTAF or bHSA:SA-DTAF complex and specific fluorochrome-conjugated monoclonal antibodies to cell surface markers along with light scatter to define specific peripheral blood cell populations.

A. Optimization of Assay Parameters for Staining of Normal Human Peripheral Blood The dose optimization of bCRP was determined by serial two-fold titration of bCRP and bHSA in HSFC from 1:25 to 1:400 on one day and from 1:20 to 1:160 on a separate day. Two individual donors were evaluated each day. The concentration of SA-DTAF was kept constant at a 1:500 dilution in HSFC (3.6 $\mu$gs). Peripheral blood monocyte binding was used to determine the optimal concentration. The percent positive values were expressed relative to the 2% cursor placed on the same population stained with the bHSA negative control. The choice of a 2% negative cursor instead of the RFI was made since a subset population was suspected due to the appearance of both a positive and negative stained monocyte population. To ensure adequate dosing the concentration of bCRP used for all experiments was kept at a 1:50 dilution representing approximately 10 $\mu$g/mL, or 1 $\mu$g/test.

A comparison of a bCRP:SA-DTAF complex to a two-step reaction, using a wash after the primary incubation of cells with bCRP, was done to ensure that the one-step method did not result in nonspecific or altered staining. The SA-DTAF was added after the primary incubation and proceeded for another 15 minutes followed by a second wash and resuspension of the cells as usual. The two-step method resulted in a similar percentage of binding (85.8 vs. 84.6%) but required ten-fold more bCRP and resulted in an approximately 20% loss of monocytes from the sample due to the extra washing. The comparison confirmed that the binding was the same in both systems. Due to the loss of monocytes with the washed two-step method, all analyses were done with the one-step bCRP: SA-DTAF complex.

The temperature incubation parameters were examined on three different donor samples stained at room temperature or placed on ice. An analysis of variance of the effect of temperature on the percentage of cells positively stained confirmed that there was a significant difference in percentage of cells binding bCRP for cells stained at room temperature compared to cells placed on ice. The non-specific binding did not increase as measured by RFI. All staining incubations were subsequently performed on ice.

Anticoagulant effects were tested on four different donor bloods that were drawn into both EDTA and heparin containing tubes. The percentage of cells binding bCRP was not significantly different between the two different anticoagulants.

The specificity of the staining was confirmed by the addition of 50 $\mu$gs of purified CRP to the cells before staining. Cells were also exposed to 10 mM EDTA, 50 $\mu$gs purified human SAP, 100 $\mu$gs PC and human IgG to confirm that results obtained using the human THP-1 cell line mimic that seen on peripheral blood monocytes. Inhibition by CRP, SAP and EDTA occurred as expected (~86%, ~77% and ~98%, respectively) with no significant inhibition by purified human IgG or PC (~6% and ~1%, respectively).

B. Multiparametric Three Color Analysis of Freshly Drawn Peripheral Blood

A total of six different normal blood samples were drawn, three individual donors on two separate occasions, and evaluated within 30–60 minutes of collection. The average percent positive values of bCRP binding on all six donors was approximately 70% of the monocytes gated by light scatter. Repetitive determinations demonstrated the intraassay precision to be 5%. One donor with a low neutrophil count and a higher than normal monocyte count, also had a higher median intensity of fluorescence even though the percent positive value for bCRP binding was similar to the other five donors. In addition this donor exhibited a higher percentage of B cells (% CD19+ lymphocytes). Other than this one donor no obvious correlation was seen with the hematology parameters (white blood count, neutrophils, lymphocytes, monocytes, granulocytes, eosinophils, basophils) or marker expression (CD4+, CD8+, CD19+, CD56+, CD13+, CD14+, CD16+, CD33+).

The flow cytometer capability of multiparametric analysis combined with monoclonal antibodies clustered by the International Workshop on Human Leukocyte Differentiation Antigens (HLDA) was used to confirm the identity of the stained cell populations. The analysis of the fresh peripheral blood samples from all six donors definitively demonstrated that bCRP was bound exclusively by monocytes as defined by known cell surface markers in combination with scatter characteristics. Histogram patterns of the six donors stained either with the negative control, bHSA: SA-DTAF, compared to cells stained with bCRP: SA-DTAF show an increase in fluorescent intensity of a cell population with the characteristic side scatter pattern of monocytes.

Scatter characteristics along with specific monoclonal antibody binding were then used to identify and select, or gate, each cell population: FSxSS, SSxCD4+CD8-PE, SSxCD19-PE, SSxCD56-PE, SSxCD16-PC5, SSxCD13-PC5, SSxCD14-PE and SSxCD33-PC5. The gated cell populations were then analyzed in conjunction with the scatter defined populations for the fluorescence intensity of bCRP: SA-DTAF staining. The fluorescent intensity of bCRP: SA-DTAF vs. events counted for each of the cell populations was compared to the negative bHSA: SA-DTAF peak in the resulting histograms. These histograms demonstrated that T cell populations gated by lymphocyte scatter and CD4+ or CD8+ staining showed no binding of bCRP above that of the negative control. NK cells selected using lymphocyte scatter and CD56+CD16+ fluorescence showed no binding of bCRP above that of the negative control. B cells identified by lymphocyte scatter and stained with CD19 showed minimal binding, <4%, of bCRP above that of the negative control. Monocytes selected by scatter and stained with either CD13, CD14 or CD33 demonstrated a definite fluorescent signal above that of the negative control. Granulocytes gated by scatter and either CD13+ or CD16+ staining showed no binding of bCRP above that of the negative control. A subset of monocytes identified by light scatter and dual CD14+CD16+ staining bound very little bCRP.

C. Multiparametric Two Color Analysis of Peripheral Blood

A series of two color panels were set up with other known monocyte markers and potential monocyte subset markers as an initial screen for subsets that might be revealed in normal peripheral blood cells. A variety of donors were used on different days with different markers, at least four donors per marker were examined except for CD11a, CD29, CD45RA and CD45RO, which were screened with a single donor. The number of donors stained and analyzed for CD13, CD14, CD16, CD32, CD33, CD64 and HLA-DR were in excess of twenty. The gating scheme used for identification was as previously described, light scatter combined with specific antibody binding. The binding pattern of bCRP:SA-DTAF occurs on the majority of monocytes that also express CD11a, CD13, CD29, CD32 and CD45RO with a consistent, small percentage of cells that are CD marker positive and do not bind CRP.

The pattern of co-expression seen with CD11b, CD14, CD33 and CD64 indicates bCRP binding to monocytes that express high levels of these markers identified by their increased fluorescent intensity. However a definite subpopulation of cells that express a lower level of these particular markers does not appear to bind bCRP. In contrast to the lack of bCRP binding seen on the subset of monocytes with dim expression of CD11b, CD14, CD33 and CD64, a population of cells was noted that are HLA-DR bright or CD11c bright and negative for bCRP binding. In addition a negative correlation was seen with the small percentage of monocytes that were positive for either CD16 or CD45RA. This subset of CD16+ or CD45RA+ monocytes bound very little, if any, bCRP.

A definite subpopulation of monocytes defined as CD14 dim/CD16 bright showed very little staining with bCRP:SA-DTAF. This subpopulation also corresponds with reduced levels of both CD33 and CD11b and increased levels of HLA-DR and has been associated with monocyte maturation, as reported in Ziegler-Heitbrock et al, 1996 *Eur. J. Immunol.*, 23(9):2053–8.

D. Binding of CRP to Peripheral Blood Monocytes from Normal Donors

Over the course of 21 months a total of 81 individual donors, consisting of 59 males and 22 females that represented a population of 53% Caucasian, 36% Hispanic, 9% Black and 2% Asian from the ages of 24 to 65 years, were evaluated for the binding of bCRP on peripheral blood monocytes by flow cytometry. Single color, two or three-color staining was used along with monocyte forward and side scatter parameters to enumerate the percentage of positively stained cells. A negative staining control, bHSA:SA-DTAF was always run to establish the negative cursor placement. The percent of peripheral blood monocytes in the sample and the percent of monocytes binding bCRP were evaluated for normality using the Kolmogorov-Smirnov Test. The values were found to be normally distributed. The samples were then evaluated for any differences in result due to gender, ethnic origin or age. No gender bias was observed for the percent of monocytes binding bCRP; no significant differences in expression in the ethnic groups were found. No significant pattern or correlation was observed between the ages of 24 to 65 years and the binding of CRP to monocytes.

CRP is bound by human peripheral blood monocytes. However, not all monocytes bound CRP. The percentage of monocytes binding bCRP was 67.9±1.3 (mean±sem) for the 81 normal donors. This value excluded any duplicate donors and included three donors that could be considered as outliers.

The necessity for calcium and the inhibition of binding by human CRP and SAP was repeated on the peripheral blood monocytes and confirmed the results obtained on the cell lines. Multiparametric analysis by flow cytometry utilizing HLDA defined antibodies to specific cell populations conclusively demonstrated the lack of binding to neutrophils and confirmed binding by monocytes. A small population of CD19+ lymphocytes bound to bCRP (less than 4%). The ability to assess the binding by such a small percentage of cells is questionable at this stage, but may point to a hitherto unknown subset of B cells. No binding was seen with the B cell line, Raji.

The use of freshly drawn peripheral blood confirmed that the lack of reactivity with neutrophils was not due to shedding or degranulation that could occur over time. Fresh peripheral blood was used with minimal disruption avoiding any damage or activation that could occur by additional isolation techniques used by other laboratories. The lack of expression on CD identified neutrophils from the six different freshly drawn donors is in direct contrast to the currently accepted paradigm The addition of PC to the assay not only confirmed that the binding to monocytes was not through CRP to a membrane exposed PC determinant but also accounted for the possibility that neutrophils might only recognize a CRP:PC complex. No indication of neutrophil binding was seen with the other 75 normal donors examined.

Flow cytometry gating strategies based on forward scatter can reduce the amount of dead or dying cells in the gate and eliminate them from further analysis. Neutrophils undergo apoptosis readily, and have a half-life in circulation of approximately 24 hours. The flip-flopped membranes characteristic of apoptotic cells expose normally hidden membrane phospholipids that can be bound by either CRP or SAP. Based on the results of this example, it appears that the reported neutrophil binding to CRP was through the exposed phospholipids on these perturbed membranes rather than by a specific receptor. It is also possible that the binding of CRP on neutrophils is markedly reduced, similar to CD14, and the assay system employed was not sensitive enough to detect the binding. However, the reported dissociation constants and sites per cell were similar to those reported for the monocyte CRP-R. In addition there was no obvious increase in granulocyte binding even in those samples that contained activated neutrophils, as demonstrated by the appearance of CD64 on their surface. CD64 is upregulated under the influence of IFNγ.

EXAMPLE 7

Multiparameter Flow Cytometric Analysis of CRP Binding to Human Peripheral Whole Blood Leukocytes in Disease States Utilizing a Functional Ligand Binding Assay Human whole blood was obtained as secondary samples from patients in a nearby hospital, and the samples were cursorily identified by an unconfirmed initial screening diagnosis (e.g. granulocytes, bands, leukemia). Actual diagnosis received two to three weeks later was then used to place samples into general categories. These categories were inflammation, cardiac, infection, cancer, hemorrhage and miscellaneous for one-of-a-kind or mixed diagnoses samples. A quantitative CRP ELISA was used to determine the concentration of plasma CRP in selected patient and normal samples. Purified human CRP and human serum albumin (HSA) were labeled with biotin and detected with a streptavidin conjugated fluorescein derivative (DTAF) as previously described. The biotin-labeled CRP:SA-DTAF along with specific fluorochrome-conjugated monoclonal antibodies to cell surface markers, were used to stain ImmunoPrep or ammonium chloride lysed whole blood from 67 patients and compared with blood from normal donors.

A. Quantitative ELISA for Plasma CRP

Plasma samples were stored at 4° C. and analyzed by a quantitative CRP ELISA on five separate occasions. A modification of the ELISA method of E. M. Macy, et al., 1997 *Clin. Chem.* 43(1):52–8 was used. RαCRP was diluted 1:1,000 in 0.01M Tris Buffer (Sigma), pH 8.0 and 100 μL (~830 ng/well) was added to each well of a microtiter plate (Nunc 96-well Immulon). The plates were incubated overnight at 4° C. then washed 1× with 0.01 M Tris-1M NaCl containing 0.1% $NaN_3$, sealed and stored at 4° C. until use.

Prior to use the plates were blocked with 200 μL PBS containing 1% BSA and 0.1% $NaN_3$ for at least one hour at room temperature. The plates were then washed with PBS-1% BSA-0.05% Tween 20 (PBT) before samples were added. Purified human CRP (>99% purity; BioDesign, Kennebunk, Me.) was used as the standard (10 μg/mL serially diluted to 0.156 μg/mL in triplicate down the columns) and plasma samples of CRP (neat, 1:5, 1:20 or 1:50 in PBT) were added (100 μL/well) in triplicate to appropriate rows. A separate control at 1.25 μg/mL was added in triplicate to assess recovery.

After addition of the samples to the microplate wells, 100 μL of biotinylated-CRP diluted 1:10,000 in PBT (5 ng/well) was added to all wells and the plates are incubated overnight at 4° C. The plates were washed 3× with PBT. Streptavidin conjugated to horseradish peroxidase (SA-HPO) was added to the plate at a dilution of 1:1,000 in PBT (100 μL/well) and the plate was placed at 25° C. with shaking for 30–60 minutes. A final 3×wash with PBT was done and 200 μL of substrate, ABTS (0.02% 2,2'-Azino-Bis-(3-Ethylbenzthiazoline-6-Sulfonic Acid) in 0.2M Sodium Citrate, pH 4.0), was added. Plates were read at 490 nm in a microplate reader using software from Molecular Devices (Softmax).

Samples that were above or below the regression curve were re-run at a different dilution to more reliably estimate the concentration. Control recoveries ranged from 3 to 20%. The average regression values for all the ELISA obtained for the 47 normal samples analyzed were similar to those reported by Macy, et al, cited above, 2.9±0.32 μg/mL (mean±sem). The majority (33/44) of the values for CRP in the patient population was above the clinical cutoff considered to be significant for inflammatory disease, 10 μg/mL. The mean±sem value obtained for the 44 patient samples tested was 55.7±13.1 μg/mL.

C. Binding of CRP to Peripheral Blood Monocytes on Normal and Patient Samples

Over the course of 21 months a total of 81 individual normal donors and 68 patient samples were evaluated for the binding of CRP to peripheral blood monocytes. Patient samples were placed into generalized, arbitrary categories for analysis once the confirmed diagnosis was obtained (see FIG. 2). The general categories used were inflammation, cardiac, cancer, infection, hemorrhage and miscellaneous. Some samples may be from the same donor such as the RA/congestive heart failure samples or the ANA/cirrhosis samples.

Figure 3:
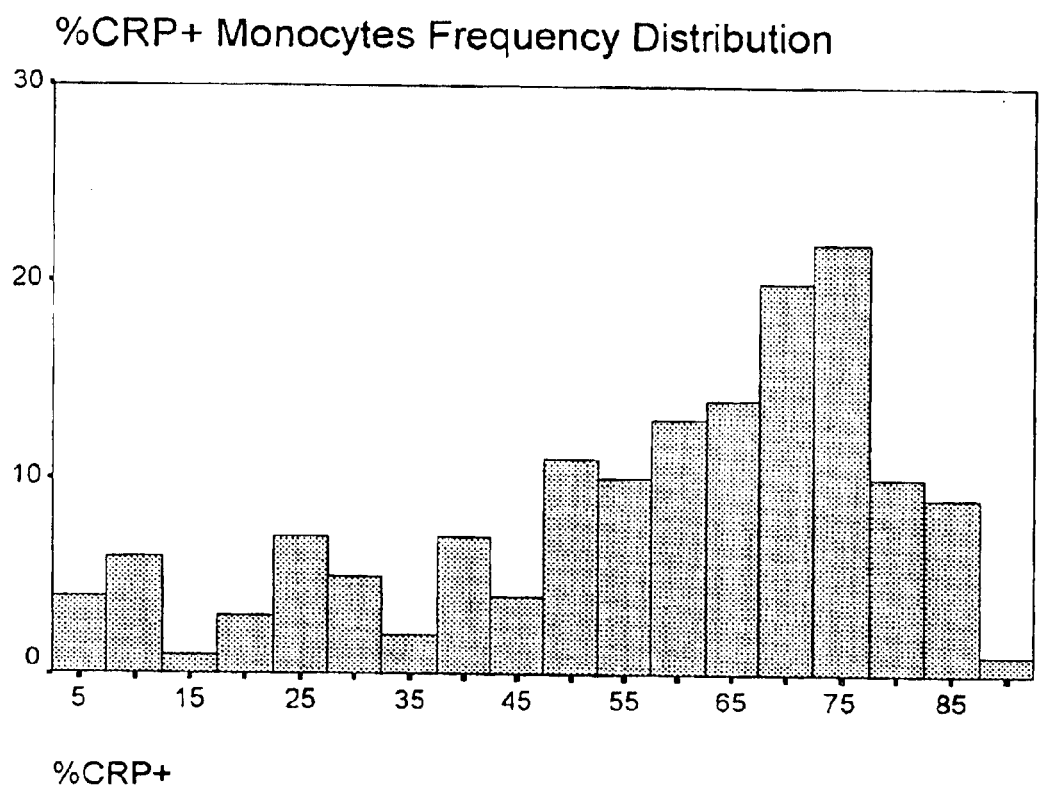
FIG. 3 is a bar graph showing the frequency distribution of the % monocytes binding bCRP for all samples tested.

The values for % CRP+ monocytes were plotted to obtain a histogram of the frequency distribution for all donors (FIG. 3). Three to four possible peaks can be visualized in the histogram. Utilizing the K-Means method to cluster the samples and detect any groupings in the data, reduced the potential for biased classification. Both 3 and 4 cluster sizes were analyzed before determining that the 4-cluster group was more descriptive of the data set. The Normals occur predominantly in cluster 2 and 3 that represent cluster centers of 75.8 and 57.8%, respectively. There are only three Normals in cluster 4 with the remainder constituting a mix of infection, cancer, inflammation and some miscellaneous samples (center=34.2). Cluster 1, with a final cluster center of 11.7%, is composed mostly of the cancer and infection categories. Cardiac and hemorrhage categorized samples occur in the Normals clusters of 2 and 3. A breakdown of the actual disease state sample categories according to cluster is shown in FIG. 4.

Figure 5A:
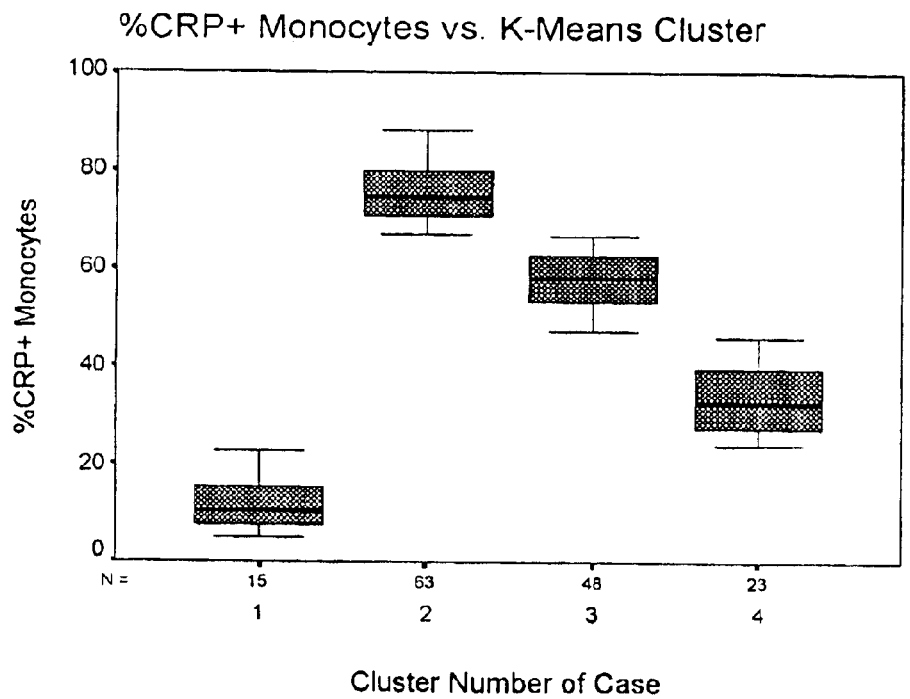
FIG. 5A is a boxplot of % CRP positive monocytes according to cluster membership. Thick lines represent the median value; boxes define the $25^{th}$ and $75^{th}$ percentiles; whiskers indicate the range of values that are not outliers.
Figure 5B:
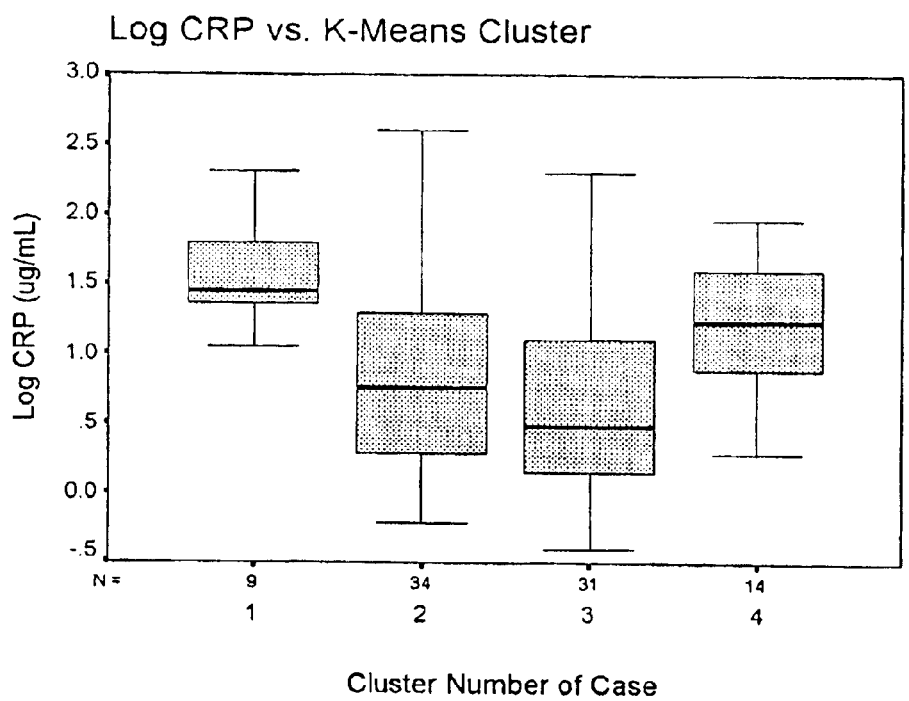
FIG. 5B is a boxplot of plasma CRP concentration according to cluster membership. Thick lines represent the median value; boxes define the $25^{th}$ and $75^{th}$ percentiles; and whiskers indicate the range of values that are not outliers.
Figure 6:
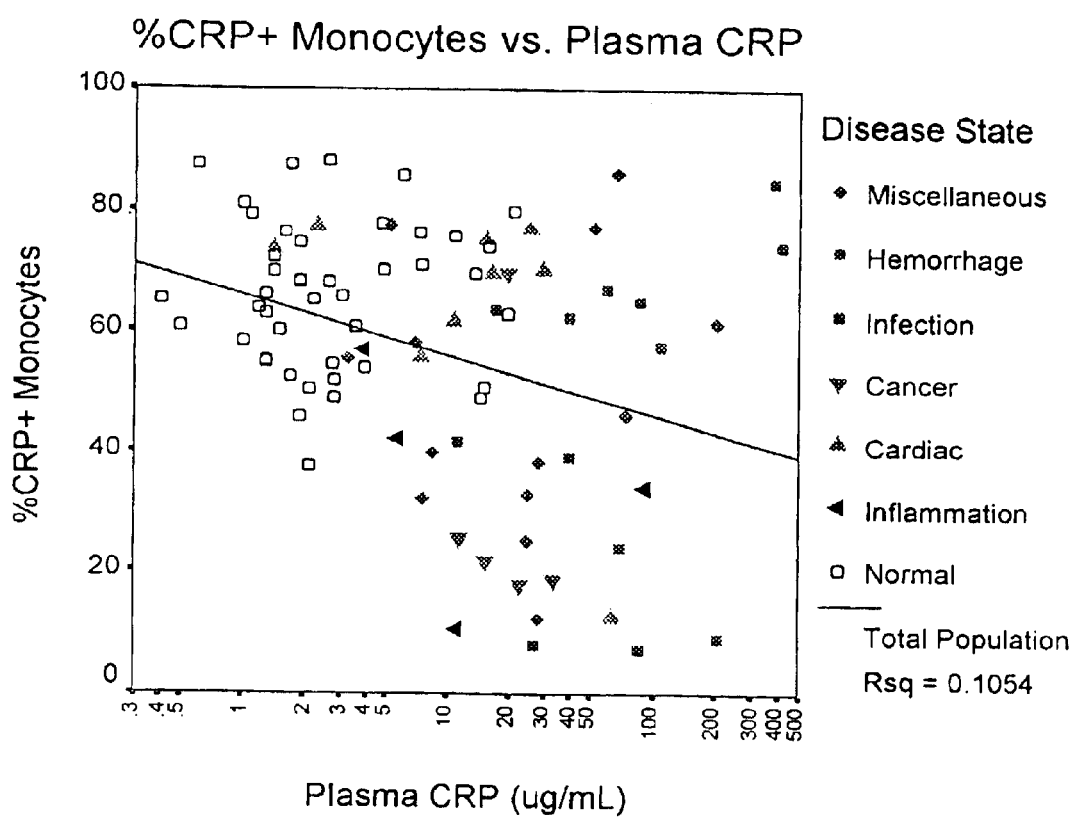
FIG. 6 is a scatterplot of % CRP positive monocytes vs. plasma CRP concentration for disease states and normals. There is little correlation between the % CRP+ monocyte values and the plasma CRP concentration (Pearson Correlation=−0.045; RSq=0.105). Though reduced level of CRP+ monocytes generally exhibits a high plasma CRP values, the reverse is not true.

The cluster centers were then used to compare the % CRP+ monocytes and the plasma CRP concentrations found in each center (FIGS. 5A and 5B). Though the highest median plasma CRP values are observed in Clusters 1 and 4, which represent the lowest % CRP+ monocytes, there is no significant correlation between the % CRP+ monocytes and plasma CRP concentration (FIG. 6). A scatterplot comparison of the % CRP expressed on monocytes to the concentration of CRP in the plasma did not give a significant Pearson Correlation or regression coefficient (Rsq=0.1054). Pearson Correlations were done on a variety of possible parameter combinations.

Figure 7:
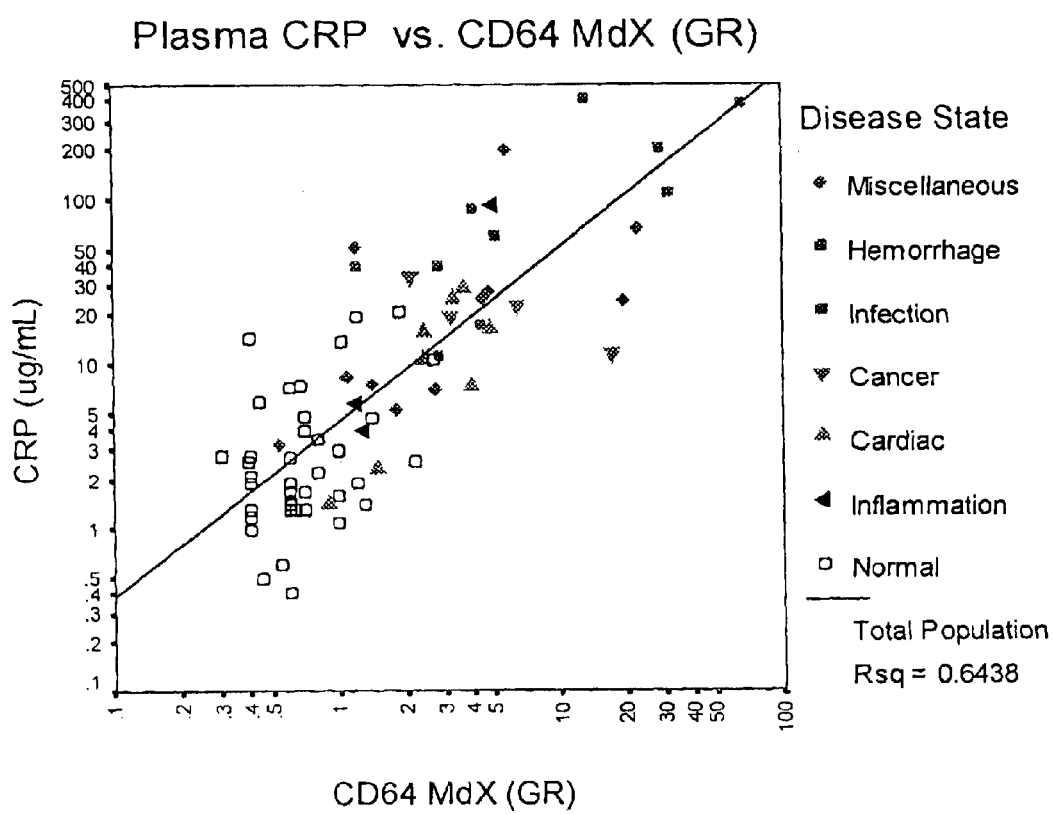
FIG. 7 shows a scatterplot and regression line of plasma CRP vs. CD64 MdX on granulocytes from diseased and normal samples. A strong correlation is observed between the upregulation of CD64 on granulocytes and the increase of CRP values in plasma.
Figure 8:
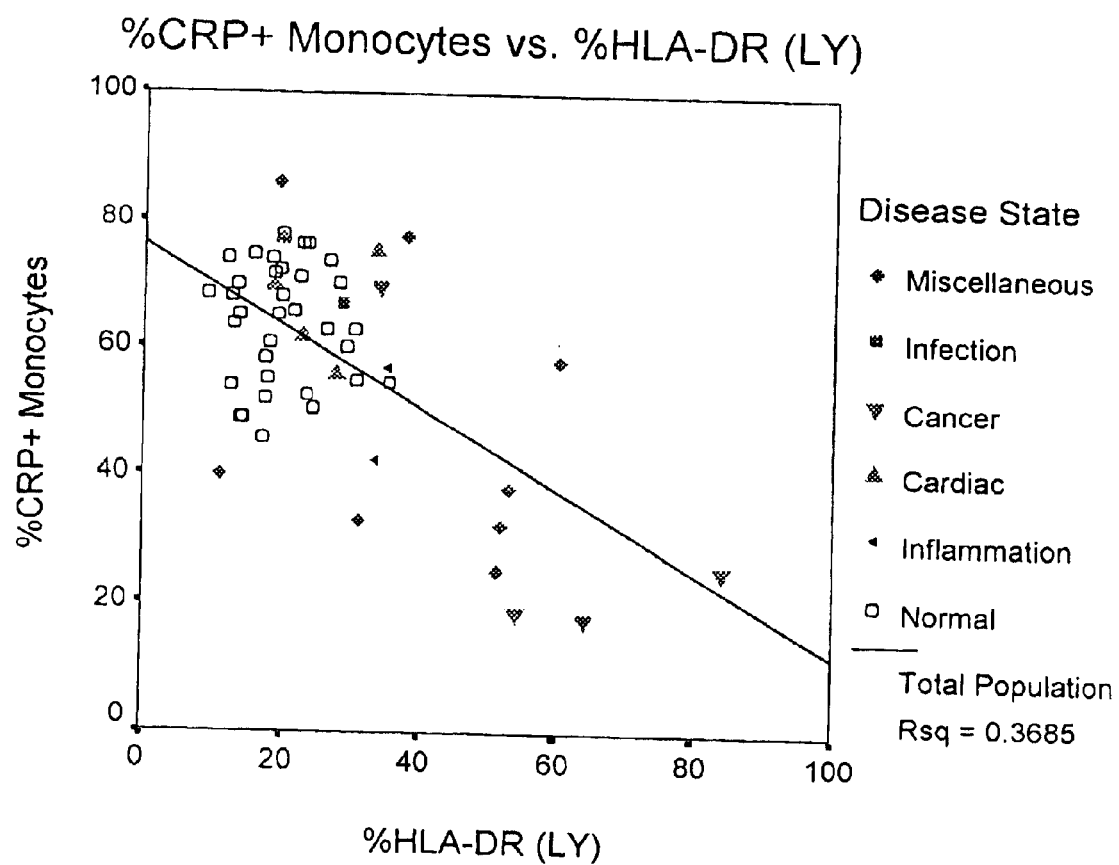
FIG. 8 shows a scatterplot and regression line of CRP+ monocytes vs. % HLA-DR expression on lymphocytes for disease states and normal.
Figure 9:
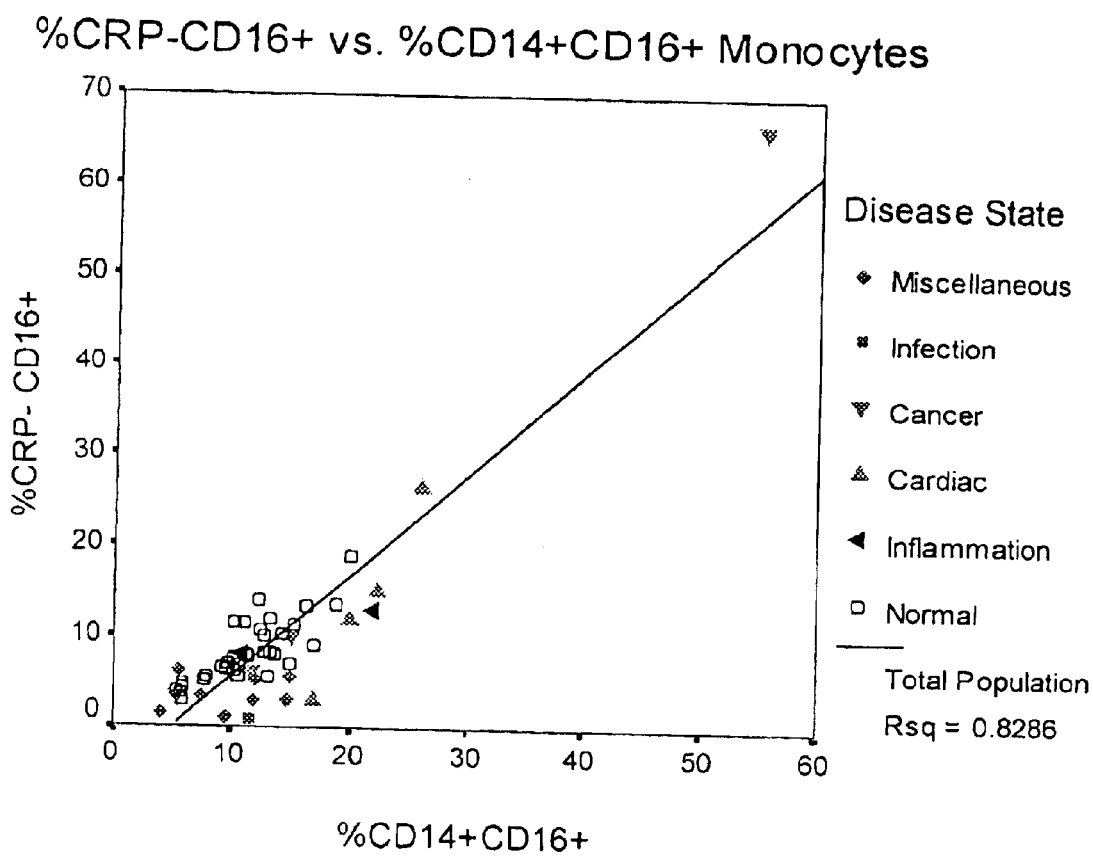
FIG. 9 shows a scatterplot and regression line comparing CRP negative binding CD16+ monocytes to the % dual positive CD14/CD16 monocytes.
Figures 10A, 10B:
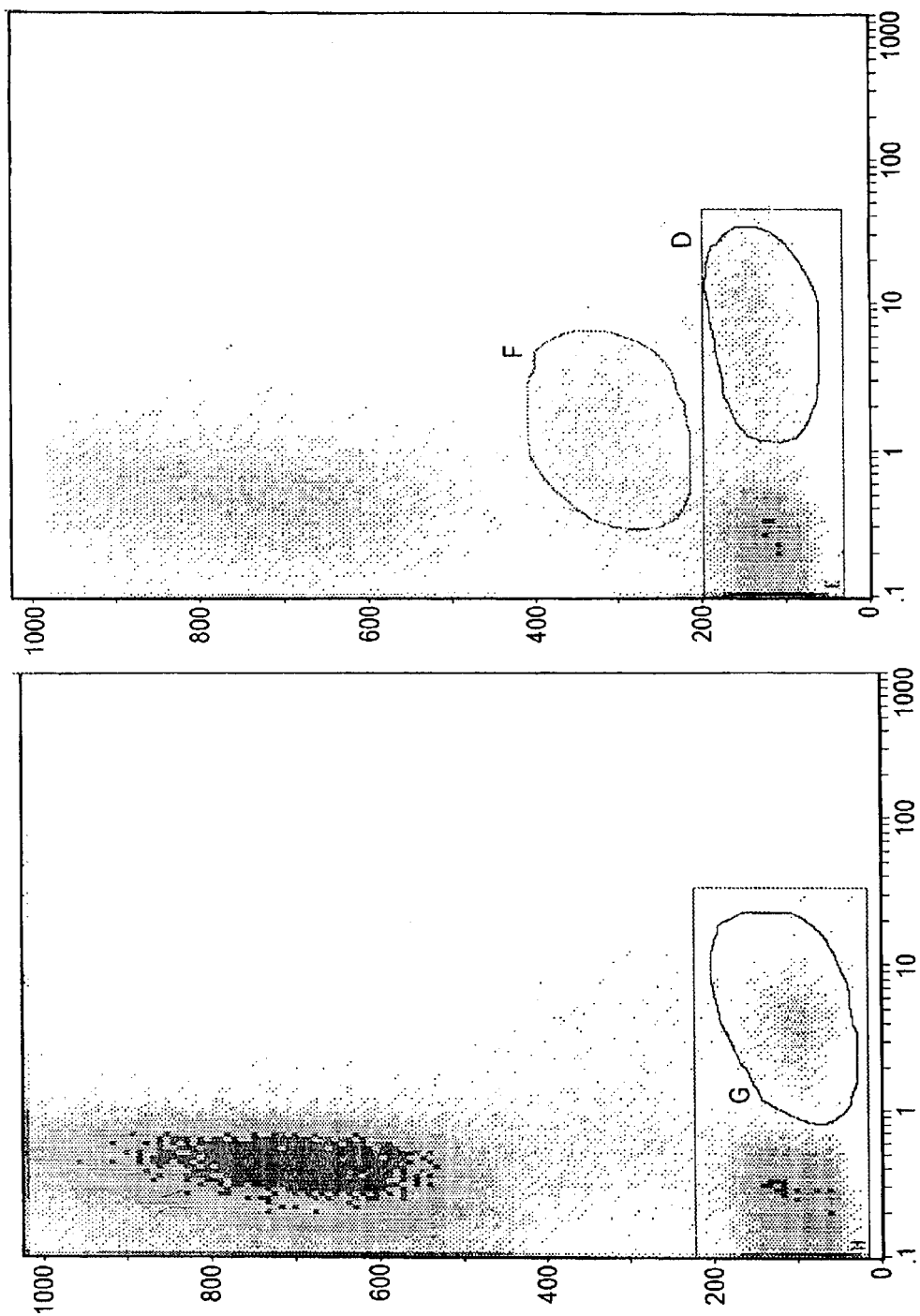

Scatterplots and regression analyses were then calculated for the various combinations and displayed according to disease state. The comparison of % CRP+ monocytes to the FcγRI receptor, CD64, on either monocytes (MdX) or granulocytes (MdX or % positive) showed no significant correlation. However, the comparison of CD64 to plasma CRP was highly significant ($p<<0.001$). The high affinity FcγRI increases on the surface of granulocytes under the influence of IFNγ. The linear regression of the scatterplot for plasma CRP and CD64 granulocyte MdX is shown along with the R-squared value of 0.644 (FIG. 7). A significant inverse correlation ($p<<0.001$) was observed between the % CRP monocyte binding compared to the % HLA-DR expression on lymphocytes on the samples tested (FIG. 8). The comparison of CRP− CD16+ monocytes to $CD14^{dim}CD16+$ monocytes demonstrates the consistent lack of CRP binding by this monocyte subset (FIG. 9). Only two SLE samples were confirmed, one with active lupus cerebritis (inflammatory) had a reduced expression. The other identified as SLE with a positive anti-nuclear antibody (ANA) had one of the highest % CRP monocyte binding values (87%). Many of the rheumatoid arthritis samples exhibited normal values of CRP binding monocytes (68±4%) but were subsequently diagnosed with congestive heart failure. One diabetes sample had normal binding pattern while a multiple sclerosis sample had decreased binding of CRP to monocytes.

Figure 1F:
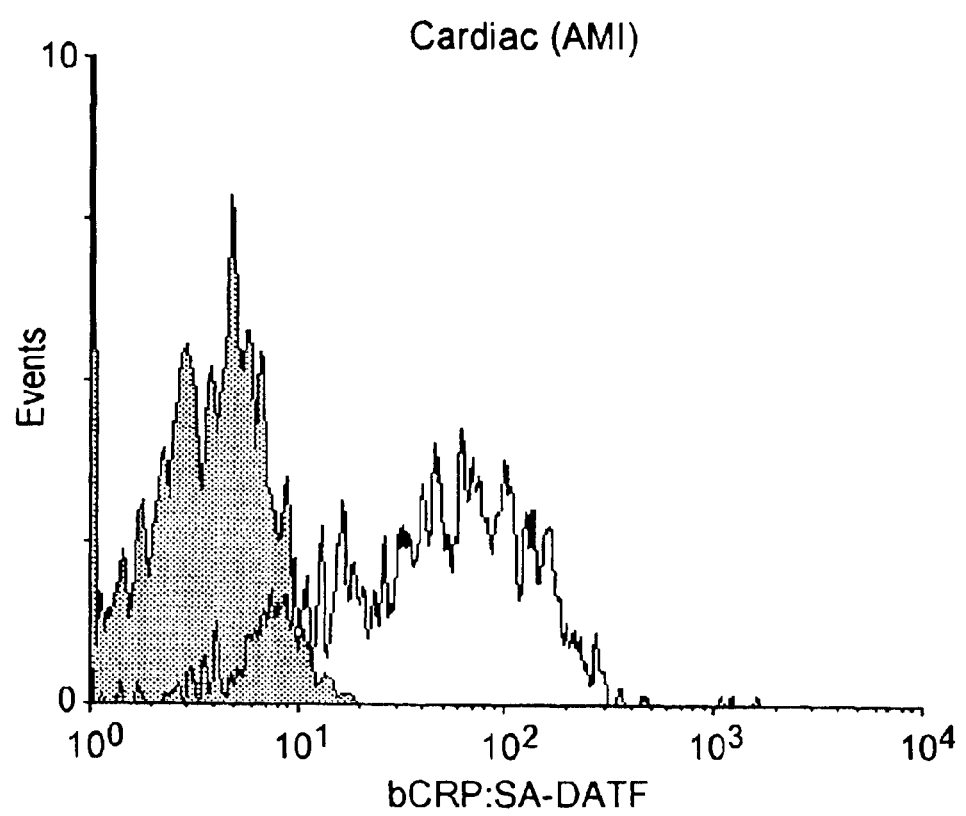
FIG. 1F is a histogram of the patient of FIG. 1D, showing monocytes (bitmapped) brought into an events vs. bCRP:SA-DTAF fluorescence histogram. Gray peak and open peak are as described for FIG. 1C.
Figure 1H:
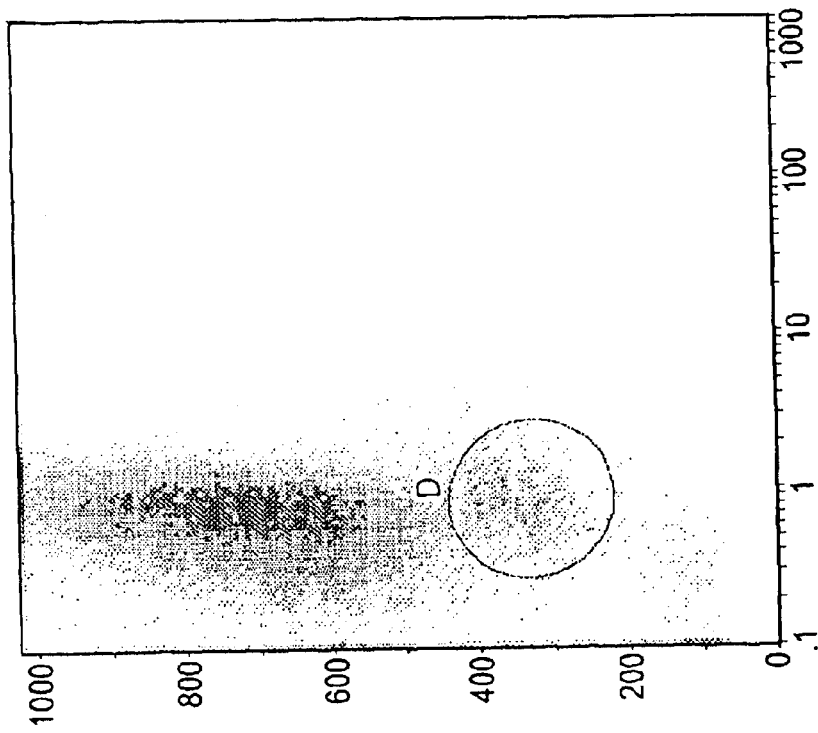
FIG. 1H is a SS vs. fluorescence histogram of the patient of FIG. 1G showing the expression of bCRP:SA-DTAF.
Figure 1G:
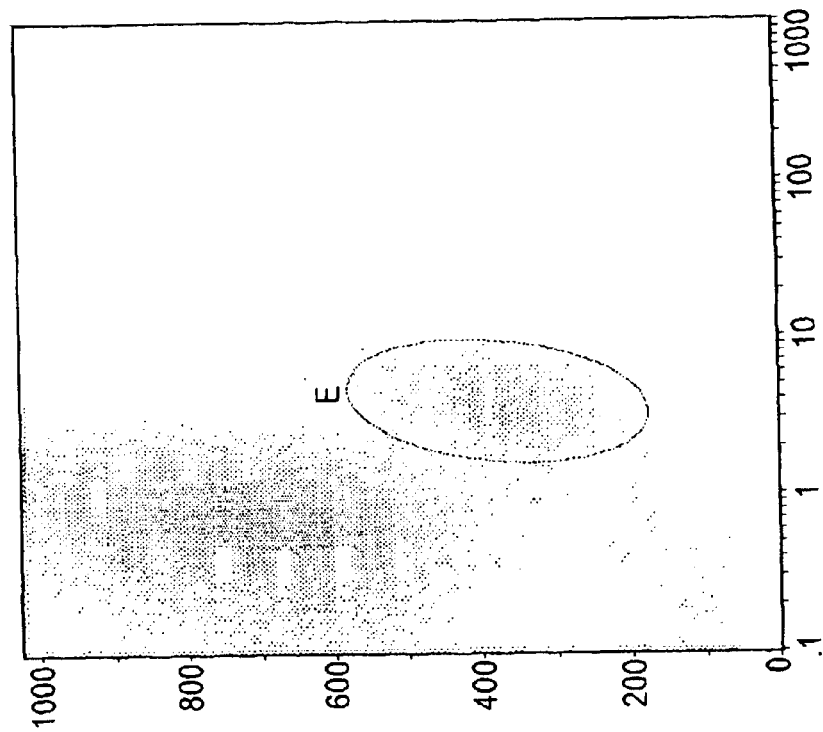
FIG. 1G is a SS vs. fluorescence histogram of a cancer patient showing expression of CD33.
Figure 1I:
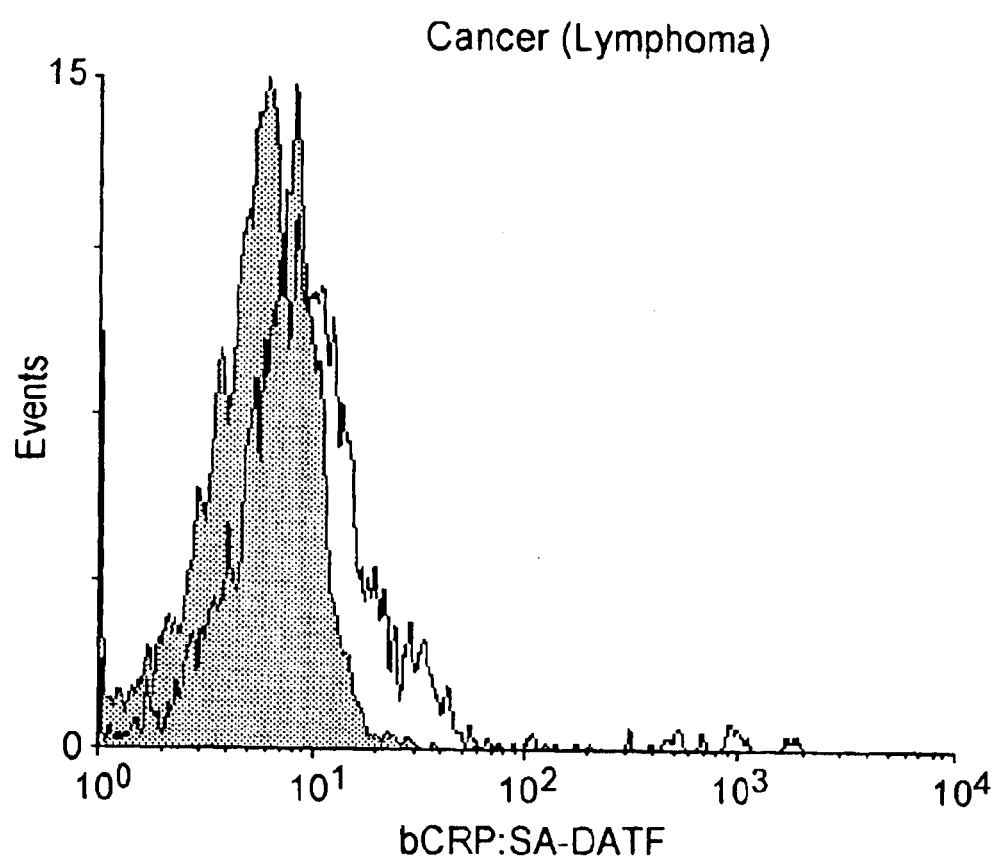
FIG. 1I is a histogram of the patient of FIG. 1G, showing monocytes (bitmapped) brought into an events vs. bCRP:SA-DTAF fluorescence histogram. Gray peak and open peak are as described in FIG. 1C.
Figure 1L:
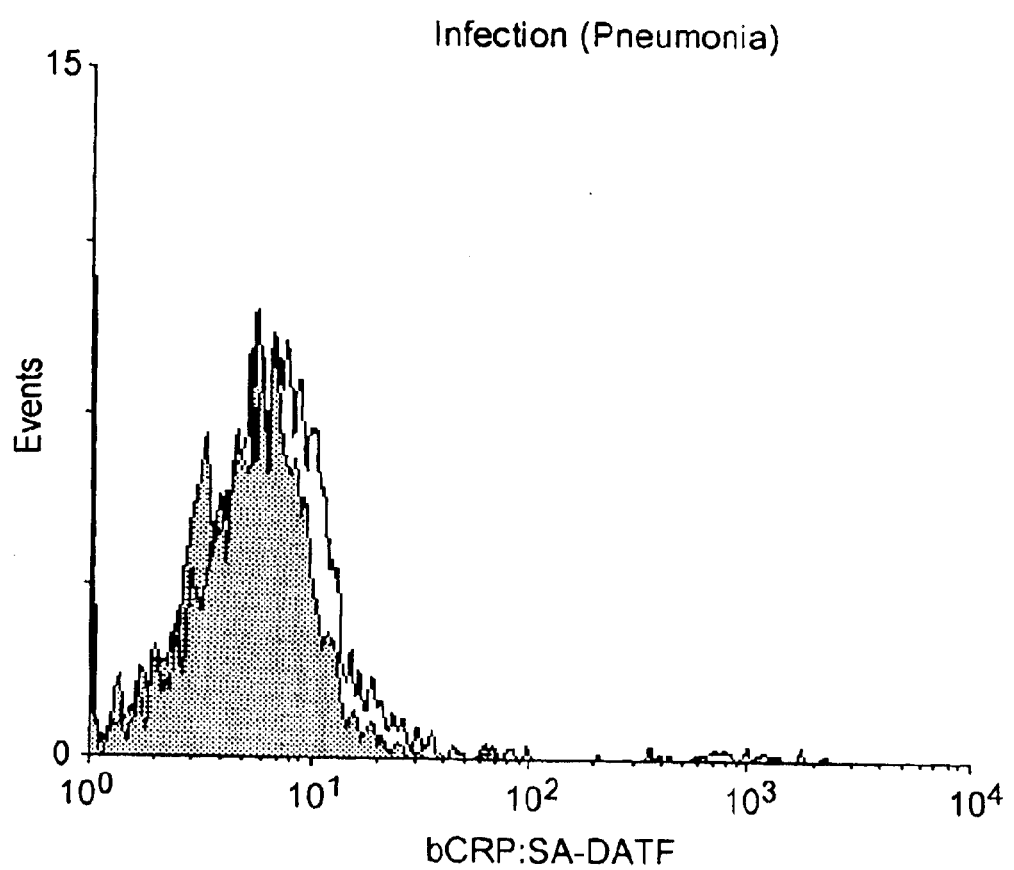
FIG. 1L is a histogram for the patient of FIG. 1J, showing monocytes (bitmapped) brought into an events vs. bCRP:SA-DTAF fluorescence histogram. Gray peak and open peak are as described in FIG. 1C.

The results of representative multiparameter histograms of the various disease states are described as follows: FIGS. 1A to 1C are representative histograms of a patient with acute pancreatitis and inflammation. The patient had a borderline low percentage of monocytes (2.8%), low binding of CRP to monocytes (10.5%), two CD33 populations and a high plasma CRP concentration of 11.2 µg/mL. FIGS. 1D to 1F are representative histograms for a patient diagnosed with myocardial infarction. The patient had a normal percentage of monocytes (5.3%), normal binding of CRP to monocytes (77.2%), no significant increase of CD64+ granulocytes above normal, and a normal plasma CRP concentration of 2.3 µg/mL. FIGS. 1G to 1I are representative histograms for a patient with lymphoma. This patient had a normal percentage of monocytes (9%), low binding of CRP to monocytes (21.6%) and a high plasma CRP concentration of 15.4 µg/mL. FIGS. 1J to 1L are representative histograms for a patient with pneumonia. This patient had a normal percentage of monocytes (3.1%), minimal binding of CRP to monocytes (7.2%), two populations of CD33 and a very high plasma CRP concentration of 85.4 µg/mL. FIGS. 1M to 1O are representative histograms for a patient with a traumatic brain hemorrhage. This patient had a normal percentage of monocytes (7.2%), normal binding of CRP to monocytes (73.9%), a significant increase of CD64+ granulocytes above normal and a very high plasma CRP concentration of 409 µg/mL. FIGS. 1P to 1S are representative histograms for a patient with SLE. This patient had a normal percentage of monocytes (3.2%), high binding of CRP to monocytes (86%), a single CD33 population, a significant increase of CD64+ granulocytes above normal and a high plasma CRP concentration of 67 µg/mL.

Figure 10:
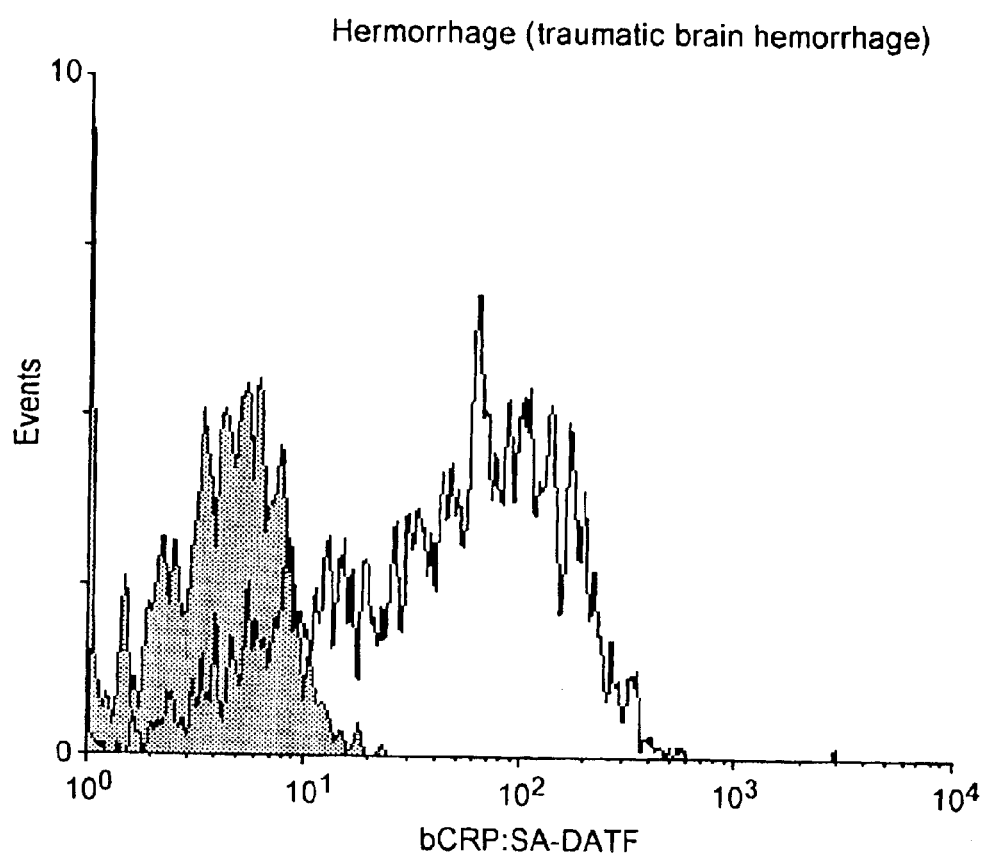
FIG. 10A is a representative histogram depicting a CRP binding cluster in the lymphocyte scatter gate. The y axis is side scatter; the x-axis is the log fluorescence of bCRP:SA-DTAF. The lymphocyte-like cluster is the amorphous defined region contained within the rectangular lymphocyte SS gate. This histogram shows an 11% cluster, with only 26% of the monocytes binding CRP.
FIG. 10B is a histogram similar to that of FIG. 10A, but containing a 10% lymphocyte-like cluster and 60% of the monocytes bind CRP.
Figure 1R:
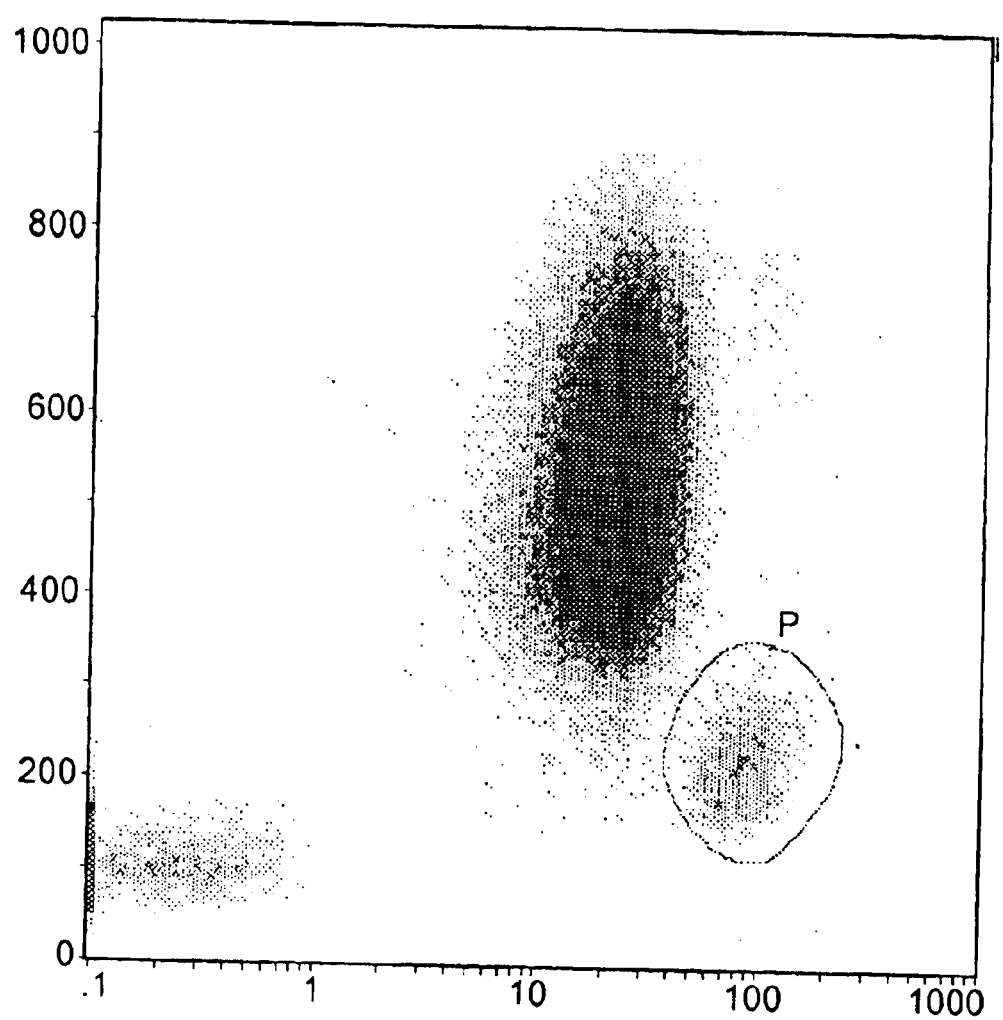
FIG. 1R is a SS vs. fluorescence histogram for the patient of FIG. 1P showing the expression of CD64.
Figure 1S:
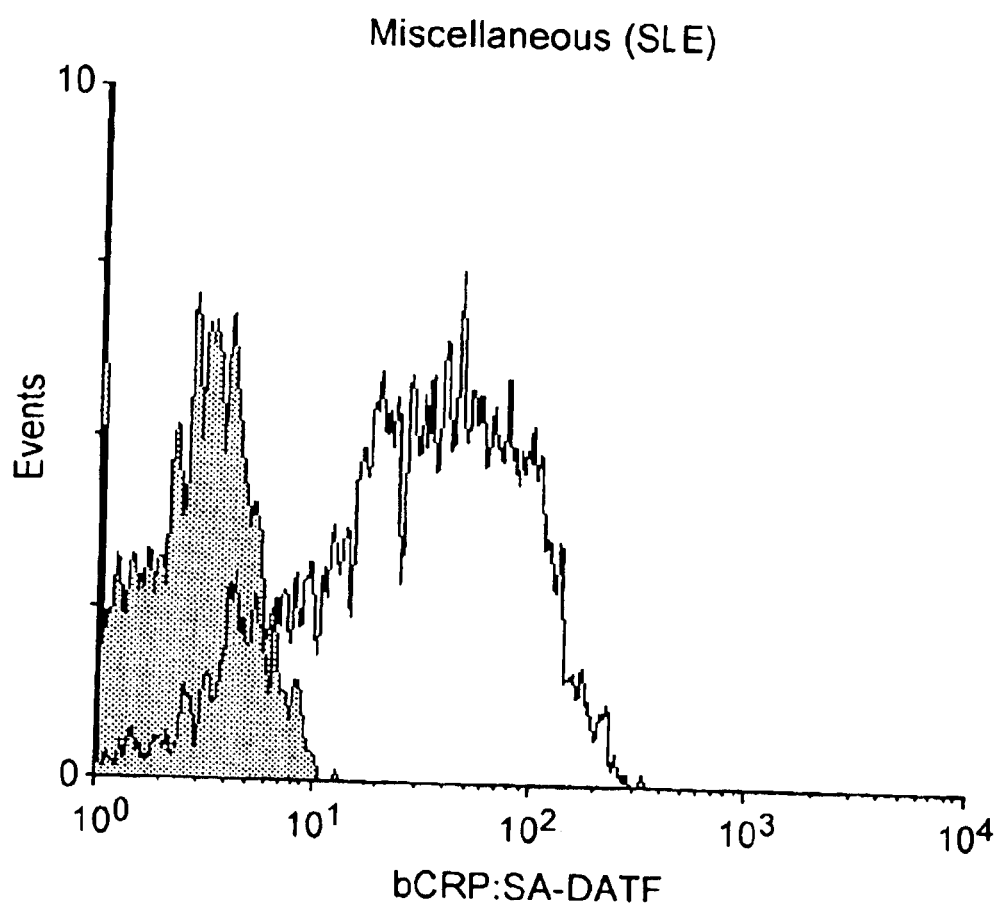
FIG. 1S is a histogram for the patient of FIG. 1P, showing monocytes (bitmapped) brought into an events vs. bCRP:SA-DTAF fluorescence histogram. Gray peak and open peak are as described in FIG. 1C.

Over the course of the evaluation there were 12 samples (2 normal, 10 patient samples) that exhibited a distinct cluster in the lymphocyte side scatter area. See FIG. 10. These were not CD14+ or CD33+ monocytes. They were less than 50% positive for HLA-DR and CD32, but one sample stained 100% with CD18 and CD45, which indicated that these were nucleated cells. Of the 10 patient samples exhibiting the lymphocyte-like cluster half were diagnosed with bacterial infection. The percent of lymphocytes in the cluster ranged from a minimum of 4% on the normal samples to a maximum of 71% on a sample with positive cultures for both P. aeruginosa and C. albicans. The percentage of monocytes binding CRP ranged from a low of 5 to a high of 84.

Specific CD markers have been used to assess the functional or maturation status of monocyte subsets. The decrease in expression of CD33 has been associated with a decreased secretion of IL-10 characteristic of mature monocytes. Dim expression of CD14 and bright expression of CD16 define another important monocyte subset. As with CD33 dim expression this monocyte subset is considered to be more mature. Interestingly, the immunophenotype of the monocyte subset that did not bind CRP consisted of the cells that were CD14+CD16+ and had low levels of CD33 indicative of more mature monocytes. CD14+/CD16+ cells are reportedly increased in a variety of inflammatory conditions such as sepsis, tuberculosis, and patients with solid tumors. The cytokine profile for the CD14+CD16+ subset is pro-inflammatory, producing IL-1, IL-6 and TNF. At this time the regulation of the putative CRP receptor is unknown, however, its appearance on monocytes that are associated with production of the IL-10 may make this anti-inflammatory cytokine a possible candidate and may prove to be important in the assessment of inflammation. Recognition of CRP or SAP by immature monocytes may be one mechanism for removing CRP or SAP complexes without triggering a potentially more damaging immune response.

The correlation between reduced CRP binding and increased lymphocyte HLA-DR also points to a possible inverse relationship with activated T cells. Resting T cells, that constitute the majority of lymphocytes, do not normally express HLA-DR. Therefore the normal level of HLA-DR (15–20%) reflects the B cell population. Any increase is due to the activation of T cells.

The results of these evaluations of CRP binding to leukocytes and plasma CRP levels in human peripheral blood of both normal and patient samples are summarized as follows. These examples support the existence of a defined cell population in human peripheral blood and on specific human-derived cell lines that reproducibly binds an evolutionarily conserved calcium-dependent conformational epitope on human CRP through a mechanism separate from its ligand, phosphorylcholine. Approximately 70% of normal peripheral blood monocytes bind CRP. The percent of monocytes binding CRP is normally distributed. The percent of CRP-binding monocytes did not correlate with the concentration of plasma CRP. The normal expression of the receptor did not show any age, gender or ethnic bias. The lack of neutrophil binding in either the patient population or the normal population confirmed the lack of CRP binding by neutrophils and substantiated the monocyte specific binding of CRP.

These examples provide evidence that the binding of CRP by monocytes is altered during certain disease states. The binding of CRP by monocytes was reduced in patient samples that were classified in the disease categories cancer, infection or inflammatory disease states. Samples diagnosed as acute myocardial infarction or congestive heart failure (cardiac), blood loss due to hemorrhage and a variety of miscellaneous states, such as surgical trauma, transplantation, abdominal pain or elevated creatinine, exhibited levels of CRP binding within the normal range of 49–90%.

This invention also provides evidence for a lack of correlation of the percent of monocytes binding CRP with the concentration of CRP in plasma. The binding of CRP to monocytes and the upregulation of the plasma protein may therefore be influenced by different cytokines. Plasma CRP is upregulated by IL-6 and IL-1 and inhibited by TNF-α. A positive correlation was observed between the concentration of plasma CRP and CD64 on granulocytes, which is upregulated by IFNγ.

In contrast to prior reports of an increase in lymphocyte-binding CRP in rheumatic fever, cancer, acute post-streptococcal glomerulitis or lymphatic filariasis, no such lymphocyte subset was determined and there was no correlation to plasma CRP. Less than 1% (12/146) of the samples in the above examples demonstrated binding to lymphocytes identified by light scatter that was above background. Of these approximately half were classified under 'infection'. The utilization of back-gating to CD14 or CD33 histograms excluded the possibility that this was due to monocyte contamination of the lymphocyte gate. These results provide evidence of an unidentified subset of lymphocytes or immune complexes.

Though there was definite correlation of plasma CRP concentration with the increased expression of FcγRI (CD64) on both monocytes and granulocytes, the correlation with percentage of monocytes binding CRP was not significant. In fact there was no binding of CRP to the upregulated CD64 on granulocytes confirming the lack of association of the CRP-R with FcγRI. Only one form of FcγRI is expressed on leukocytes negating the argument that the receptor association might be to an isoform of CD64. No binding to neutrophils was demonstrated.

Since there did not appear to be reduced levels of CRP-binding monocytes in any of the cardiac samples analyzed, the ability of these same monocytes to release tissue factor upon binding CRP may increase the potential for plaque formation at these sites. The association of CRP binding monocytes with monocyte subsets that are proposed to be upregulated by IL-10 supports a role in rapid pathogen removal.

The appearance of autoantibodies to CRP in systemic autoimmune diseases adds another proposed role for monocyte-CRP binding of these circulating CRP:anti-CRP complexes. The ability of peripheral blood monocytes to bind to these complexes may provide an important pathway for their removal from circulation with a minimum of inflammatory kickback.

A new monocyte subset is described that may further enhance the elucidation of the role innate immunity plays in the adaptive response—the existence of a receptor on monocytes has potential for immune clearance and subsequent cytokine production. The monocyte subset identified may be considered immature based on the level of expression of CD33 and the percentage of CD14+CD16+ cells. Other indirect evidence of immaturity is the lack of CRP-binding to monocytes that express CD45RA, CD11b$^{dim}$, CD64$^{dim}$, HLA-DR$^{bright}$, CD11c$^{bright}$ or CD16$_{bright}$.

Recognition of CRP via less mature monocytes may be an attempt to handle microbial invasion through natural immunity without triggering a potentially more damaging immune response or it may induce monocyte activation/maturation. The association of higher levels of IL-10 with the CRP+/CD14+/CD16−/CD33$^{bright}$ monocytes may indicate their anti-inflammatory nature. The inverse relationship of % CRP+ monocytes with activated T-cells, indicated by an increase in HLA-DR+ lymphocytes, also supports this hypothesis. The appearance of a light scatter-defined lymphocyte cluster that binds bCRP occurs predominantly, though not exclusively, in samples classified as infections and may represent circulating immune complexes.

All documents cited above are incorporated by reference herein. Also incorporated by reference is the published dissertation, R. Mills, "Multiparameter Flow Cytometric Analysis of C-Reactive Protein Binding to Human-Derived Cell Lines and Peripheral Blood Monocytes Utilizing a Functional Ligand Binding Assay", Florida International University, Miami, Fla., published Aug. 3, 2000. Numerous modifications and variations of the present invention are included in the above-identified specification and are expected to be obvious to one of skill in the art. Such modifications and alterations to the compositions and processes of the present invention are encompassed in the scope of the claims appended hereto.

What is claimed is:

1. A kit comprising:
   (a) a ligand comprising a pentraxin,
   (b) a buffer solution containing calcium ions, and
   (c) an additional ligand that binds to a moiety on particles that is not pentraxin-binding.

2. The kit according to claim 1, wherein said additional ligand is selected from the group consisting of CD64, CD14, CD16, CD45RA, CD33, CD142 and HLA-DR.

3. The kit according to claim 1, comprising a first detectable marker that labels said pentraxin and a different second detectable marker that labels said additional ligand.

4. The kit according to claim 1, further comprising a detectable marker for labeling said pentraxin ligand.

5. The kit according to claim 1, further comprising at least one component selected from the group consisting of: suitable vessels for containing samples, suitable controls or tables of normal values of pentraxin-binding receptors, instructions for using said ligand and buffer for performing said calcium-dependent assay, instructions for preparing the controls, suitable diluents and buffers for the samples, indicator charts for signal comparisons, disposable gloves, decontamination instructions, applicator sticks or containers, and sample preparator cups.

6. The kit according to claim 1, wherein said particles are of mammalian origin.

7. The kit according to claim 1, wherein said particles are of non-mammalian origin.

8. The kit according to claim 1, wherein said pentraxin is C-reactive protein (CRP).

9. The kit according to claim 1, wherein said pentraxin is selected from the group consisting of serum amyloid P (SAP), TNF-stimulated gene 14 (TSG-14) or PTX3, neuronal pentraxin 1 (NPR1), neuronal pentraxin 2 (NPR2), guinea pig apexin/p50, and rat neural activity-regulated pentraxin (narp).

10. The kit according to claim 1, wherein said particles are selected from the group consisting of leucocytes, mast cells, macrophages, progenitor cells, platelets, endothelial cells fibroblasts, neurons, microglial cells, platelets, and bacterial cells.

11. The kit according to claim 1, wherein said buffer contains calcium ions in a concentration of from 0.5 mM to 5 mM.

12. The kit according to claim 1, wherein said biological sample is selected from the group consisting of whole blood, peripheral blood, synovial fluid, cerebrospinal fluid, saliva, tissue, bone marrow, lymph node and a cell line established from mammalian cells.

13. The kit according to claim 1, wherein said level of pentraxin-binding moieties is associated with disease.

14. The kit according to claim 13, wherein said disease is selected from the group consisting of an immune disorder, an auto-immune disorder, cancer, an inflammatory disorder, sepsis and a bacterial infection.

15. The kit according to claim 14 wherein said disorder is selected from the group consisting of diabetes, multiple sclerosis, Sjorgen's Syndrome rheumatoid arthritis, and systemic lupus erythematosis.

16. The kit according to claim 1, wherein said assay is a fluorescent activated particle sorting assay.

17. A kit comprising:

(a) a ligand comprising a pentraxin, and (b) an additional ligand that binds to a moiety on particles that is not pentraxin-binding.

* * * * *